United States Patent
Akmaev et al.

(10) Patent No.: US 9,361,426 B2
(45) Date of Patent: Jun. 7, 2016

(54) COPY NUMBER ANALYSIS OF GENETIC LOCUS

(75) Inventors: Viatcheslav R. Akmaev, Brookline, MA (US); Brant Hendrickson, Shrewsbury, MA (US); Thomas Scholl, Westborough, MA (US)

(73) Assignee: ESOTERIX GENETIC LABORATORIES, LLC, Burlington, NC (US)

( * ) Notice: Subject to any disclaimer, the term of this patent is extended or adjusted under 35 U.S.C. 154(b) by 0 days.

(21) Appl. No.: 12/945,227

(22) Filed: Nov. 12, 2010

(65) Prior Publication Data

US 2011/0118145 A1 May 19, 2011

Related U.S. Application Data

(60) Provisional application No. 61/260,804, filed on Nov. 12, 2009.

(51) Int. Cl.
 *C12Q 1/68* (2006.01)
 *G06F 19/18* (2011.01)
 *G06F 19/24* (2011.01)

(52) U.S. Cl.
 CPC .............. *G06F 19/18* (2013.01); *C12Q 1/6851* (2013.01); *C12Q 1/6883* (2013.01); *C12Q 2600/112* (2013.01); *C12Q 2600/16* (2013.01); *G06F 19/24* (2013.01)

(58) Field of Classification Search
 CPC ..................... C12Q 2600/112; C12Q 2600/16; G06F 19/24
 See application file for complete search history.

(56) References Cited

U.S. PATENT DOCUMENTS

| | | | |
|---|---|---|---|
| 2008/0070792 A1 | 3/2008 | Stoughton et al. | |
| 2008/0075722 A1 | 3/2008 | DePinho et al. | |
| 2009/0215036 A1* | 8/2009 | Stropp et al. | 435/6 |
| 2012/0165202 A1* | 6/2012 | Porreca et al. | 506/2 |

FOREIGN PATENT DOCUMENTS

| | | | | |
|---|---|---|---|---|
| WO | WO 2008/078969 | * | 7/2008 | ............... C12Q 1/06 |

OTHER PUBLICATIONS

Eggermann et al., A new splice site mutation in the SMN1 gene causes discrepant results in SMN1 deletion screening approaches, Neuromuscular Disorders 18 (2008) 146-149.*
Karlen et al., Statistical significance of quantitative PCR, BMC Bioinformatics 2007, 8:131.*
Database of Genomic Variants, web page available at http://projects.tcag.ca/variation, Nov. 2, 2010.
Gibson et al., "A novel method for real time quantitative RT-PCR," Genome Research, 1996, 6:995-1001.
Haugland, Molecular Probes, handbook of Fluorescent Probes and Research Chemicals 1992-1994, 5th Ed., Molecular Probes, Inc., 1994, Table of contents only.
Heid et al., "Real time quantitative PCR," Genome Research, 1996, 6:986-994.

(Continued)

*Primary Examiner* — Reza Ghafoorian
(74) *Attorney, Agent, or Firm* — Kilpatrick Townsend & Stockton LLP

(57) ABSTRACT

Systems and methods for analyzing copy number of a target locus, detecting a disease associated with abnormal copy number of a target gene or a carrier thereof.

21 Claims, 10 Drawing Sheets

(56) References Cited

OTHER PUBLICATIONS

Iafrate et al., "Detection of large scale variation in the human genome," Nature Genetics, 2004, 36(9):949-51.
Moroni et al., "Gene copy number for epidermal growth factor receptor (EGFR) and clinical response to antiEGFR treatment in colorectal cancer: a cohort study," Lancet Oncol., 2005, 6(5):279-86.
NCBI Accession No. AC_000048.1, *Homo sapiens* chromosome 5, alternate assembly Hs_Celera, whole genome shotgun sequence, web page at http://www.ncbi.nlm.nih.gov/nuccore/AC_000048.1, as available via the Internet, Oct. 2010.
NCBI Accession No. AC_000137.1, *Homo sapiens* chromosome 5, alternate assembly HuRef, whole genome shotgun sequence, web page at http://www.ncbi.nlm.nih.gov/nuccore/AC_000137.1, as available via the Internet, Jul. 2011.
NCBI Accession No. NC_000005.9, *Homo sapiens* chromosome 5, GRCh37.p5 Primary Assembly, web page at http://www.ncbi.nlm.nih.gov/nuccore/NC_000005, as available via the Internet, Jul. 2011.
NCBI Accession No. NG_008691.1, *Homo sapiens* survival of motor neuron 1, telomeric (SMN1), RefSeqGene on chromosome 5, web page available at http://www.ncbi.nlm.nih.gov/nuccore/NG_008691.1, as available via the Internet, Nov. 2011.
NCBI Accession No. NT_006713.15, *Homo sapiens* chromosome 5 genomic contig, GRCh37.p5 Primary Assembly, web page at http://www.ncbi.nlm.nih.gov/nuccore/NT_006713.15, as available via the Internet, Jul. 2011.
NCBI Accession No. NW_001838946.1, *Homo sapiens* chromosome 5 genomic contig, alternate assembly HuRef DEGEN_1103279074318, whole genome shotgun sequence, web page at http://www.ncbi.nlm.nih.gov/nuccore/NW_001838946.1, as available via the Internet, Jul. 2011.
NCBI Accession No. NW_001841229.1, *Homo sapiens* unplaced genomic contig, alternate assembly HuRef DEGEN_1103279037052, whole genome shotgun sequence, web page at http://www.ncbi.nlm.nih.gov/nuccore/NW_001841229.1, as available via the Internet, Jul. 2011.
NCBI Accession No. NW_922707.1, *Homo sapiens* chromosome 5 genomic contig, alternate assembly Hs_Celera 211000035807261, whole genome shotgun sequence, web page at http://www.ncbi.nlm.nih.gov/nuccore/NW_922707.1, as available via the Internet, Oct. 2010.
Ouelette and Bzevanis, Bioinformatics: A Practical Guide for Analysis of Gene and Proteins, Wiley & Sons, Inc., 2nd ed., 2001.
Rashidi and Buehler, Bioinformatics Basics: Application in Biological Science and Medicine, CRC Press, London, 2000, Table of Contents only.
Salzberg et al., Computational Methods in Molecular Biology, Elsevier, Amsterdam, 1998.
Sambrook et al., "Molecular Cloning: A Laboratory Manual," 2nd Ed., 1989, Cold Springs Harbour Laboratory, Table of Content only.
Setubal et al., Introduction to Computational Biology Methods, PWS Publishing Co., Boston, 1997, Table of Content only.
SMN1 survival of motor neuron 1, telomeric [ *Homo sapiens* ], GeneID#6606, web page available at http://www.ncbi.nlm.nih.gov/nuccore?Db=gene&Cmd=retrieve&dopt=full_report&list_uids=6606&logS=databasead&logdbfrom=nuccore, as available via the Internet.
Soh et al., "Oncogene mutations, copy number gains and mutant allele specific imbalance (MASI) frequency occur together in tumor cells," PLoS One, 2009, 4(10):e7464.
Wain et al., "Genomic copy number variation, human health, and disease," Lancet, 2009, 25;374(9686):340-50. Epub 2009.
Wirth et al., "Quantitative analysis of survival motor neuron copies: identification of subtle SMN1 mutations in patients with spinal muscular atrphy, genotype-phenotype correlation, and implications for genetic counseling," Am. J. Hum. Genet., 1999, 64:1340-1356.
Zhang et al., "Copy number variation in human health, disease and evolution," Annu. Rev. Genomics Hum. Genet., 2009,10:451-81.
Zhang et al., "Development of bioinformatics resources for display and analysis of copy number and other structural variants in the humane genome," Cytogenet Genome Res., 2006,115(3-4):205-14.
Oort, P. et al., Characterization of Tusc5, an adipocyte gene co-expressed in peripheral neurons, Mol. Cell Endocrinol., 2007, 276:24-35.
State Intellectual Property Office of the People's Republic of China, Notification of the First Office Action, Application No. 201080051034, mailed Aug. 5, 2013.
Patent Cooperation Treaty, International Search Report and Written Opinion, International Application No. PCT/US10/56494, mailed Jan. 14, 2011.
Patent Cooperation Treaty, International Preliminary Report on Patentability, International Application No. PCT/US10/56494, mailed Mar. 29, 2012.
State Inellectual Property Office of the People's Republich of China, Notification of the Second Office Action, Application No. 201080051034, mailed Jun. 18, 2014.
Intellectual Property Office of Singapore, Written Opinion, Application No. 20120345-2, dated Jul. 1, 2014.
Holzapfel, B. et al., Die quantitative Real-Time-PCR (qRT-PCR). Methoden and Anwendungsgebiete, Biologie in Unserer Zeit, 37(2):120-126, 2007.
Passon, N. et al., A Simple Multiplex Real-time PCR Methodology for the SMN1 Gene Copy Number Quantification, Genetic Testing and Molecular Biomarkers, 13(1):37-42, 2009.
Pfaffl, Real-time RT-PCR: Neue Ansatze zur exakten mRNA Quantifizierung, Biospektrum 1/04, 92-95, XP055145986, 2004.
CopyCaller™ Software, User Guide, Applied Biosystems, web page at http://www6.appliedbiosystems.com/support/software/copycaller/CopyCallerUserGuide.pdf, retrieved Oct. 10, 2014, XP55145862.
European Patent Office, Extended Search report, European Application No. 10830775, dated Dec. 10, 2014.

\* cited by examiner

Genomic sequence of portion of human SMN1 gene
(Exon 7 is bolded; primers and probes are shaded)

```
(SEQ ID NO: 17)
5'  TCTGATCATA TTTTGTTGAA TAAAATAAGT AAAATGTCTT GTGAAACAAA ATGCTTTTTA    60
3'  AGACTAGTAT AAAACAACTT ATTTTATTCA TTTTACAGAA CACTTTGTTT TACGAAAAAT

SMNFUP1 primer(SEQ ID NO: 18)
    5'  CCATAT AAAGCTATCT ATATATAGCT ATCTATGT 3'
           SMN forward primer (SEQ ID NO: 19)  5'  ATAGCTAT TTTTTTTAAC
                                                      a
    ACATCCATAT AAAGCTATCT ATATATAGCT ATCTATGTCT ATATAGCTAT TTTTTTTAAC   120
    TGTAGGTATA TTTCGATAGA TATATATCGA TAGATACAGA TATATCGATA AAAAAAATTG SMN1DL Probe
(SEQ ID NO: 20)       5'  AG GGTTTcAGAC AAAATCAAAA AGAAGGAAG  3'
       TTCCTTTATT TTCC      AG GGTTTtAGAC AAAATCAAAA AGAAGGAAGG 3'  SMN2C Probe
                                        t                              (SEQ ID NO: 21)
    TTCCTTTATT TTCCTTACAG GGTTTCAGAC AAAATCAAAA AGAAGGAAGG TGCTCACATT 180
    AAGGAAATAA AAGGAATGTC CCAAAGTCTG TTTTAGTTTT TCTTCCTTCC ACGAGTGTAA
                                                       3'  ACGAGTGTAA CCTTAAATTA AGGAGTAAGT CTGCCAGCAT TATGAAAGTG AATCTTACTT TTGTAAAACT   240
    GGAATTTATT TCCTCATTCA GACGGTCGTA ATACTTTCAC TTAGAATGAA AACATTTTGA
    GGAATTTAAT TCCTCATTC  5'  SMN reverse primer (SEQ ID NO: 22)

g
    TTATGGTTTG TGGAAAACAA ATGTTTTTGA ACATTTAAAA AGTTCAGATG TTAAAAAGTT   300
    AATACCAAAC ACCTTTTGTT TACAAAAACT TGTAAATTTT TCAAGTCTAC AATTTTTCAA

GAAAGGTTAA TGTAAAACAA TCAATATTAA AGAATTTTGA TGCCAAAACT ATTAGATAAA   360
    CTTTCCAATT ACATTTGTT  AGTTATAATT TCTTAAAACT ACGGTTTTGA TAATCTATTT g
    AGGTTAATCT ACATCCCTAC TAGAATTCTC ATACTTAACT GGTTGGTTAT GTGGAAGAAA   420
    TCCAATTAGA TGTAGGGATG ATCTTAAGAG TATGAATTGA CCAACCAATA CACCTTCTTT
                                                        3'  TA CACCTTCTTT

CATACTTTCA CAATAAAGAG CTTTAGGATA TGATGCCATT TTATATCACT AGTAGGCAGA 3'  480
    GTATGAAAGT GTTATTTCTC GAAATCCTAT ACTACGGTAA AATATAGTGA TCATCCGTCT 5'
    GTATGAAAGT GTTATTTCTC 5'  SMN1RUP2 (SEQ ID NO: 23)
```

| Plate | | | | | | | |
|---|---|---|---|---|---|---|---|
| Status: Results Loaded | | | | | | | |
| LAB Action: NONE | | | | | | | |
| BIR Action: NONE | | | | | | | |

| Copy # Estimate | Copy # | Call Confidence Level | Call Confidence (Pass/Fail) | Measurement Confidence Level | Measurement Confidence (Pass/Fail) | Sample CV Level | Sample CV (Pass/Fail) | |
|---|---|---|---|---|---|---|---|---|
| 1.95 | 2 | 1 | Pass | 0.93563 | Fail | 0.19 | Fail | Details |

Reference Gene Ct

| Status | Failed Count | Wells |
|---|---|---|
| Pass | 0 | |

Reference Gene Slopes

| Status | Failed Count | Wells |
|---|---|---|
| Pass | 0 | |

Validate/Sequencing Required: No

COPY NUMBER ANALYSIS OF GENETIC LOCUS

RELATED APPLICATION

The present application claims the benefit of and priority to U.S. Provisional Application No. 61/260,804, filed on Nov. 12, 2009, the entire contents of which are incorporated by reference herein.

SEQUENCE LISTING

The present specification makes reference to a Sequence Listing (submitted electronically as a .txt file named "SeqListing.txt" on Nov. 12, 2010). The .txt file was generated on Nov. 12, 2010 and is 6 kb in size. The entire contents of the Sequence Listing are herein incorporated by reference.

BACKGROUND

The number of gene copies present in each cell of an individual can have important clinical implications. For example, an individual having less than two normal copies of an autosomal gene may be at increased risk of developing a disease and/or be a carrier for the disease. Thus, gene copy number estimates can have life-changing consequences. For example, a gene copy number estimate to determine disease carrier status can affect a couple's decision to have a child.

SUMMARY OF THE INVENTION

The present invention encompasses the recognition that diagnostic tools for determining copy numbers of a genetic locus can be improved by combining biological assays with comprehensive assessment of the quality of the biological assay measurements and/or statistical confidence of copy number calls. Thus, the present invention provides, among other things, more accurate and reliable diagnostic methods for diseases, disorders or conditions associated with abnormal copy numbers of genetic loci, or carriers thereof, with significantly reduced false-positive rate.

Thus, in one aspect, the present invention provides a method of analyzing copy number of a target locus comprising: (a) providing a plurality of biological specimens, each individual biological specimen comprising a target locus and one or more reference loci with known copy numbers; (b) performing a plurality of biological assays, wherein each individual biological assay analyzes the target locus and the one or more reference loci in the each individual biological specimen and generates detectable signals such that the level of detectable signals for the target locus and the one or more reference loci correlates with their respective copy numbers; (c) determining, based on the plurality of biological assays, a plurality of copy number estimates for the target locus normalized to the one or more reference loci; and (d) assessing quality of the copy number estimates and/or statistical confidence of the copy number call, thereby determining if a copy number call can be made for the target locus.

In some embodiments, the target locus comprises a gene or a portion thereof. In some embodiments, the target locus comprises an exon of survival motor neuron 1 (SMN1) or a portion thereof. In some embodiments, the exon of SMN1 is exon 7. In some embodiments, the one or more reference loci are selected from the group consisting of SMARCC1 and SUPT5H.

In some embodiments, the biological assays at step (b) described above are real-time PCR (RT-PCR) assays that amplify the target locus and the one or more reference loci. In some embodiments, the detectable signals are fluorescent signals, and the level of the fluorescent signals for the target locus or the one or more reference loci is detected at each amplification cycle of the RT-PCR.

In some embodiments, step (c) described above comprises steps of (i) determining the difference in cycle numbers ($\Delta Cti$) between the target locus and the one or more reference loci to reach a pre-determined level of the fluorescent signals in each individual biological specimen; (ii) generating a calibrator ($\Delta \overline{Ct}$) reflecting the difference between a normal target locus and the one or more reference loci; and (iii) determining a copy number estimate for the target locus in each individual biological specimen by normalizing the difference in the cycle numbers $\Delta Cti$ determined at step (i) to the calibrator ($\Delta \overline{Ct}$). In some embodiments, step (i) comprises first measuring cycle numbers (Cti) for each of the target locus and the one or more reference loci to reach the pre-determined level of the fluorescent signals. In some embodiments, the calibrator ($\Delta \tilde{Ct}$) is defined by trimmed mean (e.g., 80% trimmed mean) of the $\Delta Cti$ between the target locus and the one or more reference loci for the plurality of biological specimens.

In some embodiments, the copy number estimate for the target locus in each individual biological specimen is determined on a linear scale. In some embodiments, the copy number estimate for the target locus in each individual biological specimen is determined on a logarithmic scale.

In some embodiments, the quality of the copy number estimates for the target locus is assessed based on the quality of data generated for the one or more references loci. In some embodiments, the statistical confidence is assessed by determining a measurement confidence and/or a call confidence.

In some embodiments, the biological assays performed in step (b) above are replicated. In some embodiments, the statistical confidence of the copy number call is determined by the calculation of a measurement confidence for replicate biological assays and a call confidence based on the plurality of copy number estimates.

In some embodiments, step (d) above comprises determining that the copy number call for the target locus can not be made if the call confidence is less than a pre-determined threshold.

In another aspect, the present invention provides a method of detecting a disease associated with abnormal copy number of a target gene, or a carrier thereof, the method comprising (a) providing a plurality of biological specimens comprising at least one biological specimen obtained from an individual of interest; (b) performing multiple replicate biological assays on each of the plurality of biological specimens to analyze the target gene and one or more reference genes with known copy numbers, wherein each of the multiple replicate biological assays generates detectable signals such that the level of the detectable signals for the target gene and the one or more reference genes correlates with their respective copy numbers; (c) determining copy number estimates for the target gene normalized to the one or more reference genes; and (d) assessing quality of the copy number estimates and/or statistical confidence of a copy number call for the individual of interest, thereby determining if the copy number call for the target gene in the individual can be made. In some embodiments, inventive methods of the present invention further comprises a step of determining if the individual has or is at risk for the disease, or if the individual is a carrier of the disease. In some embodiments, the disease is Spinal Muscular Atrophy (SMA). In some embodiments, the target gene is survival motor neuron 1 (SMN1).

In some embodiments, the biological assays performed at step (b) above are real-time PCR assays. In some embodiments, step (b) above comprises performing real-time PCR assays that amplify at least a portion of exon 7 of SMN1. In some embodiments, the detectable signals generated by biological assays are fluorescent signals, and the level of the fluorescent signals for the target gene or the one or more reference genes is detected at each amplification cycle of the RT-PCR.

In some embodiments, step (c) above comprises steps of (i) determining the difference in the cycle numbers ($\Delta$Cti) between the target gene and the one or more reference genes to reach a pre-determined level of the fluorescent signals in each individual replicate assay; (ii) generating a calibrator ($\Delta \overline{C}t$) reflecting the background difference between a normal target gene and the one or more reference genes; and (iii) generating a copy number estimate based on each individual replicate assay by normalizing the difference in the cycle numbers $\Delta$Cti determined at step (i) to the calibrator ($\Delta \overline{C}t$).

In some embodiments, the copy number estimate for the target gene based on each individual replicate assay is determined on a linear scale. In some embodiments, the copy number estimate for the target gene based on each individual replicate assay is determined on a logarithmic scale.

In some embodiments, assessing the quality of the copy number estimates comprises generating quality control metrics based on cycle number measurements and the amplification curve slope thereof generated for the one or more reference genes. In some embodiments, assessing the quality of the copy number estimates comprises determining coefficient of variation between the multiple replicate biological assays. In some embodiments, assessing the statistical confidence of the copy number call comprises determining a measurement confidence and/or a call confidence. In some embodiments, the statistical confidence of the copy number call is determined by the calculation of a measurement confidence for the multiple replicate biological assays and a call confidence based on a plurality of copy number estimates.

In some embodiments, the measurement confidence is determined as the largest normal confidence interval around the copy number estimates defined by the mean of the copy number estimates across the multiple replicate assays and the standard error of the mean that fits within predetermined copy number limits. In some embodiments, step (d) above comprises determining that the copy number call can not be made if the measurement confidence does not exceed a pre-determined confidence threshold.

In some embodiments, the call confidence determines t-test p-values for the copy number estimate's being from adjacent copy number distributions. In some embodiments, step (d) comprises determining that the copy number call can not be made if the call confidence is less than a pre-determined confidence threshold.

In some embodiments, inventive methods of the present invention further comprises analyzing, in parallel, one or more control samples with pre-determined copy numbers of the target gene.

In some embodiments, biological assays on the plurality of biological specimens and the one or more control samples are conducted on a multi-well plate (e.g., 96-well or 384-well plate). In some embodiments, inventive methods of the present invention further comprises determining plate quality control metrics based on the quality control and statistical analysis of the one or more control samples. In some embodiments, the plate is failed if any of the one or more control samples fails one of the quality control or statistical confidence assessment or if an estimate for any individual control sample does not equal to the pre-determined copy number.

In some embodiments, a biological specimen suitable for the present invention comprises nucleic acid from cells, tissue, whole blood, plasma, serum, urine, stool, saliva, cord blood, chorionic villus sample, chorionic villus sample culture, amniotic fluid, amniotic fluid culture, or transcervical lavage fluid. In some embodiments, a biological specimen suitable for the invention is a prenatal sample.

In yet another aspect, the present invention provides systems for analyzing copy number of a target locus as described herein. In some embodiments, a system according to the invention comprising: a) means to receive a plurality of biological specimens, wherein each individual biological specimen comprises a target locus and one or more reference loci with known copy numbers; b) means to carry out a plurality of biological assays, wherein each individual biological assay analyzes the target locus and the one or more reference loci in each individual biological specimen and generates detectable signals such that the level of detectable signals for the target locus and the one or more reference loci correlates with their respective copy numbers; c) a determination module configured to detect the detectable signals from each individual biological specimen, and to determine the level of the detectable signals; d) a storage device configured to store signal information from the determination module; e) a computing module adapted to (i) calculate copy number estimates for the target locus normalized to the one or more reference loci based on the signal information stored on the storage device and (ii) determine the quality of the copy number estimates and/or statistical confidence of the copy number call; and f) a display module for displaying a content based in part on the computing and data analysis result for the user, wherein the content comprises a copy number call for the target locus and/or a signal indicating if any of the quality control or statistical confidence analysis is failed. In some embodiments, the target locus comprises an exon of survival motor neuron 1 (SMN1) or a portion thereof.

In some embodiments, the biological assays are real-time PCR assays. In some embodiments, the determination module is configured to determine the level of the detectable signals at each amplification cycle and the detectable signals are fluorescent signals.

In some embodiments, the computing module is adapted to calculate copy number estimates for the target locus according to the following steps: (i) determining the difference in the cycle numbers ($\Delta$Cti) between the target locus and the one or more reference loci to reach a pre-determined level of the fluorescent signals in each individual specimen; (ii) generating a calibrator ($\Delta \overline{C}t$) reflecting the background difference between a normal target locus and the one or more reference loci; and (iii) determining a copy number estimate for the target locus in each individual biological specimen by normalizing the difference in the cycle numbers $\Delta$Cti determined at step (i) to the calibrator ($\Delta \overline{C}t$).

In some embodiments, the computing module is adapted to determine the quality of the copy number estimates by at least generating quality control metrics based on cycle number measurements and the amplification curve slope thereof generated for the one or more reference genes. In some embodiments, the computing module is adapted to determine the quality of the copy number estimates by at least determining sample coefficient of variation. In some embodiments, the computing module is adapted to determine statistical confidence of the copy number call by at least determining a measurement confidence and compare the determined measurement confidence to a pre-determined threshold limit. In some embodiments, the computing module is adapted to determine statistical confidence of the copy number call by at least determining a call confidence and compare the determined call confidence to a pre-determined threshold limit. In some embodiments, the computing module is further adapted to determine if any control sample is failed.

In still another aspect, the present invention provides computer readable media having computer readable instructions recorded thereon to define software modules including a computing module and a display module for implementing a method on a computer as described herein. In some embodiments, said method comprising: a) calculating, with the computing module, (i) copy number estimates for a target locus normalized to one or more reference loci based on real-time PCR data stored on a storage device and (ii) the quality of the copy number estimates and/or statistical confidence of the copy number call; and b) displaying a content based in part on the computing and data analysis result for the user, wherein the content comprises a copy number call for the target locus and/or a signal indicating if any of the quality control or statistical confidence analysis is failed. In some embodiments, the target locus comprises exon 7 of SMN1 or a portion thereof.

In yet another but related aspect, the present invention provides diagnostic kits for detecting diseases, disorders or conditions associated with abnormal copy number or allelic variants of a genetic locus, or carriers thereof, using compositions and methods as described herein. In some embodiments, inventive kits according to the invention are suitable for diagnosis of Spinal Muscular Atrophy (SMA) or a carrier thereof. In some embodiments, a kit according to the invention contains (a) one or more reagents for amplifying exon 7 of SMN1 or a portion thereof; (b) one or more reagents for amplifying one or more reference loci with known copy numbers; and (c) a computer readable medium described herein.

In this application, the use of "or" means "and/or" unless stated otherwise. As used in this application, the term "comprise" and variations of the term, such as "comprising" and "comprises," are not intended to exclude other additives, components, integers or steps. As used herein, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value unless otherwise stated or otherwise evident from the context (except where such number would exceed 100% of a possible value).

Other features, objects, and advantages of the present invention are apparent in the detailed description, drawings and claims that follow. It should be understood, however, that the detailed description, the drawings, and the claims, while indicating embodiments of the present invention, are given by way of illustration only, not limitation. Various changes and modifications within the scope of the invention will become apparent to those skilled in the art.

BRIEF DESCRIPTION OF DRAWINGS

Drawings are for illustration purposes only, and not for limitations.

FIG. 1 depicts the genomic sequence of a portion of the SMN1 gene comprising exon 7. The sequence encoding exon 7 is bolded. Exemplary primers and probes that could be used in TAQMAN™ analysis are shown (shaded). Exemplary sequencing primers (SMNFUP1 and SMNRIP1) are also depicted (shaded). Lower case letters indicate single nucleotide polymorphisms.

FIGS. 6A-B are screen shots depicting an embodiment of a layout for displaying specimen and plate statistics and the results of plate and specimen quality control.

DEFINITIONS

Figure 2:
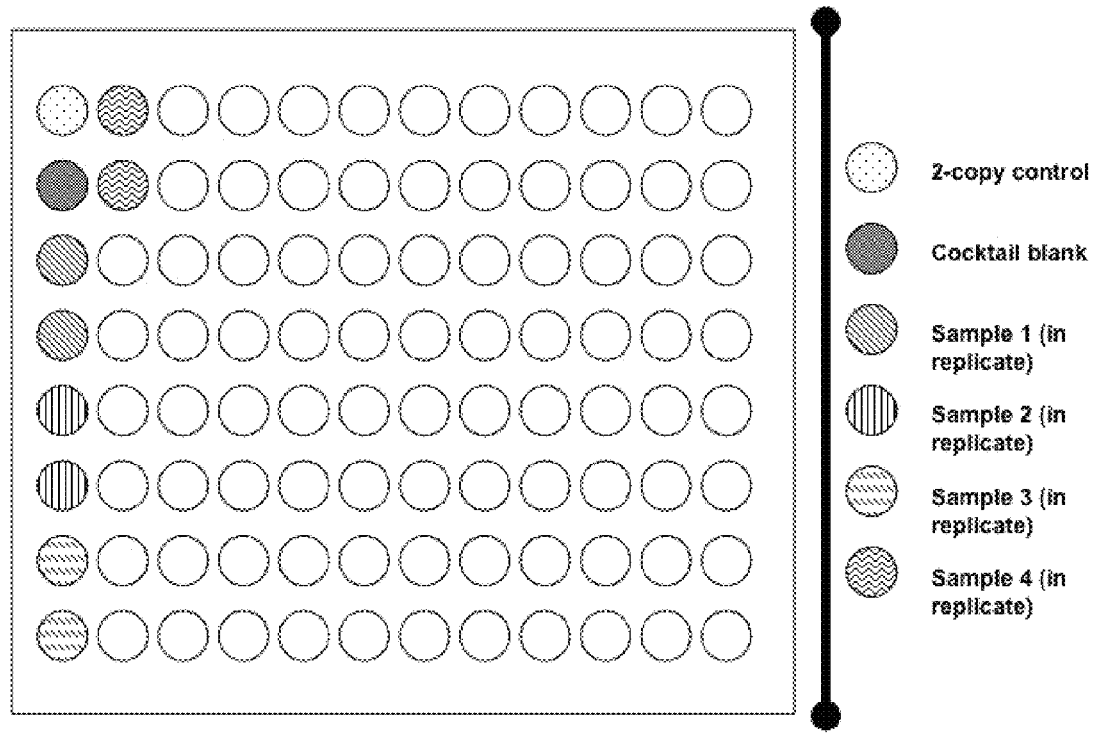
FIG. 2 depicts an exemplary plate format, in which wells containing a 2-copy control, a cocktail (e.g. of reagents and buffer) blank, and samples in replicate, are shown.

In order for the present invention to be more readily understood, certain terms are first defined below. Additional definitions for the following terms and other terms are set forth throughout the specification.

As used herein, the phrase "allele" is used interchangeably with "allelic variant" and refers to a variant of a locus or gene. In some embodiments, a particular allele of a locus or gene is associated with a particular phenotype, for example, altered risk of developing a disease or condition, likelihood of progressing to a particular disease or condition stage, amenability to particular therapeutics, susceptibility to infection, immune function, etc.

As used herein, the phrase "biological specimen" is used interchangeably with "biological sample" and may be referred to as "specimen" or "sample". The phrase "biological specimen" as used herein refers to any solid or fluid (or combination thereof) sample obtained from, excreted by or secreted by any living cell or organism. In certain embodiments, biological specimens comprise nucleic acids. Non-limiting examples of biological specimens include blood, plasma, serum, urine, stool, saliva, cord blood, chorionic villus samples, amniotic fluid, and transcervical lavage fluid. Cell cultures of any biological specimens can also be used as biological specimens, e.g., cultures of chorionic villus samples and/or aminoitic fluid cultures such as amniocyte cultures. A biological specimen can also be, e.g., a sample obtained from any organ or tissue (including a biopsy or autopsy specimen), can comprise cells (whether primary cells or cultured cells), medium conditioned by any cell, tissue or organ, tissue culture. In some embodiments, replicates of the same specimen may be assayed. (See "replicates" below.)

As used herein, the phrase "carrier" refers to an individual that harbors a genetic mutation or allelic variant but displaying no symptoms of a disease associated with the genetic mutation or allelic variant. A carrier, however, is typically able to pass the genetic mutation or allelic variant onto their offspring, who may then express the mutated gene or allelic variant. Typically, this phenomenon is a result of the recessive nature of many genes. In certain embodiments, the mutation or allelic variant that the carrier harbors predisposes or is associated with a particular phenotype, for example, altered risk of developing a disease or condition, likelihood of progressing to a particular disease or condition stage, amenability to particular therapeutics, susceptibility to infection, immune function, etc. Without limitation, a carrier may have reduced or increased copy numbers of a gene or a portion of a gene. A carrier may also harbor mutations (e.g., point mutations, polymorphisms, deletions, insertions or translocations, etc.) within a gene. A "carrier" is also referred to as a "genetic carrier" herein.

As used herein, the phrase "copy number" when used in reference to a locus, refers to the number of copies of such a locus present per genome or genome equivalent. A "normal copy number" when used in reference to a locus, refers to the copy number of a normal or wild-type allele present in a normal individual. In certain embodiments, the copy number ranges from zero to two inclusive. In certain embodiments, the copy number ranges from zero to three, zero to four, zero to six, zero to seven, or zero to more than seven copies, inclusive. In embodiments in which the copy number of a locus varies greatly across individuals in a population, an estimated median copy number could be taken as the "normal copy number" for calculation and/or comparison purposes.

As used herein, the term "gene" refers to a discrete nucleic acid sequence responsible for a discrete cellular (e.g., intracellular or extracellular) product and/or function. More specifically, the term "gene" refers to a nucleic acid that includes a portion encoding a protein and optionally encompasses regulatory sequences, such as promoters, enhancers, terminators, and the like, which are involved in the regulation of expression of the protein encoded by the gene of interest. As used herein, the term "gene" can also include nucleic acids that do not encode proteins but rather provide templates for transcription of functional RNA molecules such as tRNAs, rRNAs, etc. Alternatively, a gene may define a genomic location for a particular event/function, such as a protein and/or nucleic acid binding site.

The terms "individual" and "subject" are used herein interchangeably. As used herein, they refer to a human or another mammal (e.g., mouse, rat, rabbit, dog, cat, cattle, swine, sheep, horse or primate) that can be afflicted with or is susceptible to a disease or disorder (e.g., spinal muscular atrophy) but may or may not display symptoms of the disease or disorder. In many embodiments, the subject is a human being. In many embodiments, the subject is a patient. Unless otherwise stated, the terms "individual" and "subject" do not denote a particular age, and thus encompass adults, children (e.g., toddlers or newborns) and unborn infants.

As used herein, the term "locus" refers the specific location of a particular DNA sequence on a chromosome. As used herein, a particular DNA sequence can be of any length (e.g., one, two, three, ten, fifty, or more nucleotides). In some embodiments, the locus is or comprises a gene or a portion of a gene. In some embodiments, the locus is or comprises an exon or a portion of an exon of a gene. In some embodiments, the locus is or comprises an intron or a portion of an intron of a gene. In some embodiments, the locus is or comprises a regulatory element or a portion of a regulatory element of a gene. In some embodiments, the locus is associated with a disease, disorder, and/or condition. For example, mutations at the locus (including deletions, insertions, splicing mutations, point mutations, etc.) may be correlated with a disease, disorder, and/or condition.

As used herein, the term "normal," when used to modify the term "copy number" or "locus" or "gene" or "allele," refers to the copy number or locus, gene, or allele that is present in the highest percentage in a population, e.g., the wild-type number or allele. When used to modify the term "individual" or "subject" they refer to an individual or group of individuals who carry the copy number or the locus, gene or allele that is present in the highest percentage in a population, e.g., a wild-type individual or subject. Typically, a normal "individual" or "subject" does not have a particular disease or condition and is also not a carrier of the disease or condition. The term "normal" is also used herein to qualify a biological specimen or sample isolated from a normal or wild-type individual or subject, for example, a "normal biological sample."

As used herein, the term "probe," when used in reference to a probe for a nucleic acid, refers to a nucleic acid molecule having specific nucleotide sequences (e.g., RNA or DNA) that can bind or hybridize to nucleic acids of interest. Typically, probes specifically bind (or specifically hybridize) to nucleic acid of complementary or substantially complementary sequence through one or more types of chemical bonds, usually through hydrogen bond formation. In some embodiments, probes can bind to nucleic acids of DNA amplicons in a real-time PCR reaction.

As used herein, the term "replicate" when used in reference to a biological assay refers to a duplicate assay or repeat assay conducted to improve reliability, fault-tolerance or to facilitate statistic analysis. In some embodiments, the term "replicate" is used interchangeably with the phrase "replicate assay" or "replicate biological assay". Typically, replicate assays are done using materials from the same or similar biological specimen taken from the same individual. That is, multiple specimens may be obtained from a particular individual, and/or a single specimen from a particular individual may be divided into parts (each part being used in a replicate assay or stored for later use). In some embodiments, the number of replicate assays used is chosen depending on predetermined statistical thresholds or empirically. In some embodiments, duplicates, triplicates, quadruplicates, pentuplicates, sextuplicates, septuplicates, octuplicates, nonuplicates, decuplicates, or more than 10 replicates are used. In some embodiments, quadruplicates are used.

As used herein, the term "signal" refers to a detectable and/or measurable entity. In certain embodiments, the signal is detectable by the human eye, e.g., visible. For example, the signal could be or could relate to intensity and/or wavelength of color in the visible spectrum. Non-limiting examples of such signals include colored precipitates and colored soluble products resulting from a chemical reaction such as an enzymatic reaction. In certain embodiments, the signal is detectable using an apparatus. In some embodiments, the signal is generated from a fluorophore that emits fluorescent light when excited, where the light is detectable with a fluorescence detector. In some embodiments, the signal is or relates to light (e.g., visible light and/or ultraviolet light) that is detectable by a spectrophotometer. For example, light generated by a chemiluminescent reaction could be used as a signal. In some embodiments, the signal is or relates to radiation, e.g., radiation emitted by radioisotopes, infrared radiation, etc. In certain embodiments, the signal is a direct or indirect indicator of a property of a physical entity. For example, a signal could be used as an indicator of amount and/or concentration of a nucleic acid in a biological sample and/or in a reaction vessel.

DETAILED DESCRIPTION

The present invention provides more accurate and reliable methods for analyzing genetic loci. Among other things, the present invention provides methods for analyzing copy numbers of a genetic locus (in particular, a normal genetic locus) by combining biological assays with comprehensive quality control and statistical confidence assessment. As described in the Examples section, the inventors of the present application have successfully developed systems and methods to effectively and efficiently combine biological and statistical analysis. In some embodiments, the invention utilizes an algorithm, executable by a computer system, that assesses the quality of copy number estimates by determining, for example, measurement confidence for the biological assays and the statistical confidence for the copy number call. In some embodiments, inventive methods disclosed herein analyze a target locus together with one or more reference loci with known copy numbers using same biological assays (e.g., real-time PCR) to facilitate quality control and/or statistical confidence assessment.

A number of genetic loci are implicated in genetic diseases, and such loci may be analyzed using methods disclosed herein. Thus, methods disclosed herein can facilitate detection of carriers, diagnosis of patients, prenatal diagnosis, and/or genotyping of embryos for implantation, etc. As appreciated by those of ordinary skill in the art, the genetic disease with which a target locus is associated can follow any of a number of inheritance patterns, including, for example, autosomal recessive, autosomal dominant, sex-linked dominant, and sex-linked recessive.

In some embodiments, copy number analysis is performed on a locus for which deletion of part or all of the locus is implicated in a disease. Deletions at target loci include, but are not limited to, deletions of sizes of less than 20 base pairs (bp), between 20 bp and 100 bp inclusive, between 100 bp and 200 bp inclusive, between 200 bp and 500 bp inclusive, between 500 bp and 1 kb inclusive, between 1 kb and 2 kb inclusive, between 2 kb and 5 kb inclusive, between 5 kb and 10 kb inclusive, between 10 kb and 20 kb inclusive, between 20 kb and 30 kb inclusive, and greater than 30 kb.

In some embodiments, copy number analysis is performed on a target locus for which one or more point mutations and/or insertion mutations is implicated in a disease. In these cases, biological assays may be designed to detect the copy number of the normal sequence or allele present at the target locus. For example, methods such as real time PCR can be adapted using primers that discriminate between mutations and normal nucleotide sequence such that amplification only occurs when the normal sequence is present.

Various aspects of the invention are described in detail in the following sections. The use of sections is not meant to limit the invention. Each section can apply to any aspect of the invention. In this application, the use of "or" means "and/or" unless stated otherwise.

I. Target Loci and Associated Genetic Diseases, Disorders and Conditions

Inventive methods according to the present invention are suitable for analyzing copy number of any target locus. In certain embodiments, a target locus is associated with a disease, disorder or condition. For example, a mutation or allelic variation at or within a target locus may be correlated with an altered (e.g., increased or decreased) risk of developing a disease, disorder or condition and/or status as a carrier thereof. In some embodiments, there is a causal relationship between the mutation or allelic variation at or within the target locus and the disease, disorder or condition or carrier status. In some embodiments, the mutation or allelic variation at or within the target locus may co-segregate with the disease, disorder or condition but not directly contribute to the development of the disease, disorder or condition In some embodiments, a target locus that can be analyzed according to the present invention comprises a gene or portion thereof (e.g., exon, intron, promoter or other regulatory region). Table 1 lists non-limiting examples of such genes and associated genetic diseases, disorders or conditions. As understood by one of ordinary skill in the art, a gene may be known by more than one name. The listing in Table 1 does not exclude the existence of additional genes that may be associated with a particular disease. The present invention encompasses those additional genes including those that will be discovered in the future associated with each particular diseases.

TABLE 1

Exemplary genes associated with genetic diseases, disorders or conditions

| Disease, Disorder or condition | Gene | Protein Product |
|---|---|---|
| Achondroplasia | FGFR3 | fibroblast growth factor receptor 3 |
| Adrenoleukodystrophy | ABCD1 | ATP-binding cassette (ABC) transporters |
| Alpha-1-antitrypsin deficiency | SERPINA1 | serine protease inhibitor |
| Alpha-thalassemia | HBA 1&2 | hemoglobin alpha 1 &2 |
| Alport syndrome | COL4A5 | collagen, type IV, alpha 5 |
| Amyotrophic lateral sclerosis | SOD1 | superoxide dismutase 1 |
| Angelman syndrome | UBE3A | ubiquitin protein ligase E3A |
| Ataxia telengiectasia | ATM | ataxia telangiectasia mutated |
| Autoimmune polyglandular syndrome | AIRE | autoimmune regulator |
| Bloom syndrome | BLM, RECQL3 | recQ3 helicase-like |
| Burkitt lymphoma | MYC | v-myc myelocytomatosis viral oncogene homolog |
| Canavan disease | ASPA | aspartoacylase |
| Congenital adrenal hyperplasia | CYP21 | cytochrome P450, family 21 |
| Cystic fibrosis | CFTR | cystic fibrosis transmembrane conductance regulator |
| Diastrophic dysplasia | SLC26A2 | sulfate transporter |
| Duchenne muscular dystrophy | DMD | Dystrophin |
| Familial dysautonomia | IKBKAP | IKK complex-associated protein (IKAP) |
| Familial Mediterranean fever | MEFV | Mediterranean fever protein |
| Fanconi anemia | FANCA, FANCB (FAAP95), | (proteins involved in DNA repair) |

TABLE 1-continued

Exemplary genes associated with genetic diseases, disorders or conditions

| Disease, Disorder or condition | Gene | Protein Product |
|---|---|---|
| | FANCC, FANCD1 (BRCA2), FANCD2, FANCE, FANCF, FANCG, FANCI, FANCJ (BRIP1), FANCL (PHF9 and POG), FANCM (FAAP250) | |
| Fragile X syndrome | FMR1 | fragile X mental retardation 1 |
| Friedrich's ataxia | FRDA | Frataxin |
| Gaucher disease | GBA | glucosidase |
| Glucose galactose malabsorption | SGLT1 | sodium-dependent glucose cotransporter |
| Glycogen disease type I (GSD1) | G6PC (GSDIa) | glucose-6-phosphatase |
| | SLC37A4 (GSDIb) | glucose-5-phosphate transporter 3, solute carrier family 37 member 4 |
| Gyrate atrophy | OAT | crnithine aminotransferase |
| Hemophilia A | F8 | hoagulation factor VIII |
| Hereditary hemocrhomatosis | HFE | hemochromatosis protein |
| Huntington disease | HD | Tuntingtin |
| Immunodeficiency with hyper-IgM | TNFSF5 | humor necrosis factor member 5 |
| Lesch-Nyhan syndrome | HPRT1 | hypoxanthine phosphoribotransferase |
| Maple syrup urine disease (MSUD) | BCKDHA | branched chain keto acid dehydrogenase |
| Marfan syndrome | FBN1 | Fibrillin |
| Megalencephalic leukoencephalopathy | MLC1 | (putative transmembrane protein) |
| Menkes syndrome | ATP7A | ATPase Cu++ transporting |
| Metachromatic leukodystrophy (MLD) | ARSA | arylsulfatase A |
| Mucolipidosis IV (ML IV) | MCOLN1 | Mucolipin-1 |
| Myotonic dystrophy | DMPK | myotonic dystrophy protein kinase |
| Nemaline myopathy | | |
| Neurofibromatosis | NF1, NF2 | neurofibromin |
| Niemann Pick disease (types A and B type) | SMPD1 | sphingomyelin phosphodiesterase 1, acid lysosomal (acid sphingomyelinase) |
| Niemann Pick disease (type C) | NPC1, NPC2 | Niemann-Pick disease, type C1 (an integral membrane protein) and Niemann-Pick disease, type C2 |
| Paroxysmal nocturnal hemoglobinuria | PIGA | phosphatidylinositol glycan |
| Pendred syndrome | PDS | Pendrin |
| Phenylketonuria | PAH | phenylalanine hydroxylase |
| Refsum disease | PHYH | Phytanoyl-CoA hydroxylase |
| Retinoblastoma | RB | retinoblastoma 1 |
| Rett syndrome | MECP2 | methyl CpG binding protein |
| SCID-ADA (Severe combined immunodeficiency-ADA) | ADA | adenosine deaminase |
| SCID-X-linked (Sever combined immunodeficiency-X-linked) | IL2RG | Interleukin-2-receptor, gamma |
| Sickle cell anemia (also known as beta-thalassemia) | HBB | hemoglobin, beta |
| Spinal muscular atrophy (SMA) | SMN1, SMN2 | survival of motor neuron 1, Survival of motor neuron 2 |
| Tangier disease | ABCA1 | ATP-binding cassette A1 |
| Tay-Sachs disease | HEXA | hexosaminidase |
| Usher syndrome (Also known as Hallgren syndrome, Usher-Hallgren syndrome, rp-dysacusis syndrome and dystrophia retinae dysacusis syndrome.) | MYO7A | myosin VIIA |
| | USH1C | Harmonin |
| | CDH23 | cadherin 23 |
| | PCDH15 | protocadherin 15 |
| | USH1G | SANS |
| | USH2A | Usherin |
| | GPR98 | VLGR1b |
| | DFNB31 | Whirlin |
| | CLRN1 | clarin-1 |

TABLE 1-continued

Exemplary genes associated with genetic diseases, disorders or conditions

| Disease, Disorder or condition | Gene | Protein Product |
|---|---|---|
| Von Hippel-Lindau syndrome | VHL | elongin binding protein |
| Werner syndrome | WRN | Werner syndrome protein |
| Wilson's disease | ATP7B | ATPase, Cu++ transporting |
| Zellweger syndrome | PXR1 | peroxisome receptor 1 |

Thus, target loci that can be analyzed using inventive methods of the present invention include, but are not limited to, genes identified in Table 1, or a portion thereof (e.g., exon, intron, or regulatory region). The sequences of the genes identified in Table 1 are known in the art and are readily accessible by searching in public databases such as GenBank using gene names and such sequences are incorporated herein by reference.

Although most genes are normally present in two copies per genome equivalent, a large number of genes have been found for which copy number variations exist between individuals. Copy number differences can arise from a number of mechanisms, including, but not limited to, gene duplication events, gene deletion events, gene conversion events, gene rearrangements, chromosome transpositions, etc. Differences in copy numbers of certain genes may have implications including, but not limited to, risk of developing a disease or condition, likelihood of progressing to a particular disease or condition stage, amenability to particular therapeutics, susceptibility to infection, immune function, etc. In addition to the genes listed in Table 1, methods disclosed herein are suitable for analyzing copy numbers at loci with such copy number variants. The Database of Genomic Variants, which is maintained at the website whose address is "http://" followed immediately by "projects.tcag.ca/variation" (the entire contents of which are herein incorporated by reference in their entirety), lists more than at least 38,406 copy number variants (as of Mar. 11, 2009). (See, e.g., Iafrate et al. (2004) "Detection of large-scale variation in the human genome" *Nature Genetics*. 36(9):949-51; Zhang et al. (2006) "Development of bioinformatics resources for display and analysis of copy number and other structural variants in the human genome." 115(3-4):205-14; Zhang et al. (2009) "Copy Number Variation in Human Health, Disease and Evolution," *Annual Review of Genomics and Human Genetics*. 10:451-481; and Wain et al. (2009) "Genomic copy number variation, human health, and disease." Lancet. 374:340-350, the entire contents of each which are herein incorporated by reference).

SMN1, SMN2 and Spinal Muscular Atrophy (SMA)

In some embodiments, a target locus is the gene Survivor of Motor Neuron 1 (SMN1), or a portion (e.g., an exon) of SMN1. A partial human genomic sequence of SMN1 is depicted in FIG. 1 (For information about human SMN1, see, e.g., GeneID #6606 in the EntrezGene database at the National Center for Biotechnology Information (NCBI), at the website whose address is "http" followed immediately by www.ncbi.nlm.nih.gov/nuccore?Db=gene&Cmd=retrieve&dopt=full_report&list_uids=6606 &log$-databasead&logdbfrom=nuccore, the entire contents of which are herein incorporated by reference. Exemplary partial or whole genomic sequences for human SMN1 can be found in the NCBI nucleotide database under accession numbers NG_008691.1, NC_000005.9, NT_006713.15, AC_000048.1, NW_922707.1, AC_000137.1, NW_001838946.1, and NW_001841229.1.)

SMN1 is part of a duplicated region on chromosome 5q13, and mutations in SMN1 are associated with spinal muscular atrophy (SMA), which is an untreatable autosomal recessive disorder that affects motor neurons in the anterior horn of the spinal cord. With a carrier frequency between 1:50 and 1:30, SMA is the second most common lethal autosomal recessive disease in the Western hemisphere after cystic fibrosis.

About ninety-four percent of all SMA patients lack exon 7 of the SMN1 gene in both alleles. It was thought that both gene deletion and gene conversion events may have attributed to the lack of exon 7 in SMN1 in SMA patients. In some embodiments, inventive methods of the present invention analyze copy number of part or all of exon 7 of SMN1. See FIG. 1 for a genomic sequence of exon 7 of SMN1.

A related gene, Survivor of Motor Neuron 2 (SMN2) is located near SMN1 on chromosome 5q13 and encodes a homolog of SMN1. Although the coding sequence of SMN2 differs by a single nucleotide (840 C→T) in exon 7, SMN2 gene product cannot compensate fully for loss of SMN1. Without being held to theory, the translationally silent C→T transition at position 840 in SMN2 is thought to decrease the activity of an exonic splicing enhancer such that a truncated transcript is generated. The truncated transcript is thought to be unstable and rapidly degraded in the cell. Although SMN2 gene product cannot compensate fully for loss of SMN1, some recent research suggests that SMN2 could be a modifier of SMN1. In some embodiments, the present invention can be used to analyze gene SMN2, or a portion (e.g., exon) of SMN2.

Tumor Suppressor Genes and/or Oncogenes

In some embodiments, the target locus is a gene, or portion of a gene (e.g., exon) implicated in cancer, such as a tumor suppressor gene and/or oncogene. For example, epidermal growth factor 1 (EGFR) is an oncogene whose copy number varies between individuals. EGFR copy number can be higher than normal in cancers such as non-small cell lung cancer and may have implications for amenability to cancer therapies. In addition to copy number variation, there are a number of mutational variants of EGFR, such as deletions of exons 2-7 of EGFR. Examples of other or additional oncogenes whose copy numbers may be estimated using methods of the present invention include, but are not limited to, B-raf oncogene (BRAF); K-ras oncogone (KRAS); and Phosphatidylinositol 3-kinase, catalytic, alpha (PIK3CA). Examples of tumor suppressor genes whose numbers may be estimated using methods of the present invention include, but are not limited to, phosphatase and tensin homolog (PTEN). (See, e.g., Moroni et al. (2005), "Gene copy number for epidermal growth factor receptor (EGFR) and clinical response to antiEGFR treatment in colorectal cancer: a cohort study." *Lancet Oncol.* 6(5):279-86.); and Soh et al. (2009) "Oncogene mutations, copy number gains and mutant allele specific imbalance (MASI) frequently occur together in tumor cells." 4(10): e7464., the entire contents of each of which are herein incorporated by reference.)

Genes Involved in Susceptibility to Infection

In some embodiments, the target locus is a gene, or portion of a gene (e.g., exon) involved in susceptibility to infection. In some embodiments, the target locus is the gene, or a gene portion (e.g., exon) of CCL3L1. CCL3L1 is located on the q-arm of chromosome 17 and its copy number varies among individuals. Most individuals have one to six copies per diploid genome, and some individuals have no copies or more than six copies. Increased CCL31 copy number has been associated with lower susceptibility to human HIV infection. CCL31 encodes a cytokine that binds to several chemokine receptors including chemokine binding protein 2 and chemokine (C-C motif) receptor 5 (CCR5). CCR5 is a co-receptor for HIV, and binding of CCL3L1 to CCR5 inhibits HIV entry.

Genes Involved in Regulating Immune Function

In some embodiments, the target locus is a gene, or portion of a gene (e.g., exon) involved in regulating immune function. In some embodiments, the target locus is FCGR3B, which encodes a CD16 surface immunoglobulin receptor. Low copy number of FCGR3B is correlated with increased susceptibility to systemic lupus erythematosus and similar inflammatory autoimmune disorders. Variation in copy number of FCGR3B has also been found to be associated with autism, schizophrenia, and idiopathic learning disability.

II. Reference Loci

According to the present invention, one or more references loci are typically analyzed along with a target locus using same biological assays. Copy numbers of reference loci are known or pre-determined using the same biological assays. Typically, suitable reference loci have stable copy numbers and are unlikely to change between different biological specimens. The data generated for the reference loci may be used to normalize the copy number estimates for the target locus and/or to facilitate assessment of the quality of the copy number estimates and/or statistical confidence with respect to the assay measurement.

In some embodiments, the copy number of a reference locus is the same as the normal copy number of the target locus. In some embodiments, the copy number of a reference locus is greater than the normal copy number of the target locus. In some embodiments, the copy number of a reference locus is less than the normal copy number of the target locus. In some embodiments, a reference locus and a target locus are on the same chromosome. In some embodiments, a reference locus and a target locus are on different chromosomes.

Any of a variety of loci with known copy numbers may be used as a reference locus. In some embodiments, one reference locus can be SMARCC1 (SWI/SNF related, matrix associated, actin dependent regulator of chromatin, subfamily c, member 1), or suppressor of Ty 5 homolog (SUPTSH), or a portion thereof.

In some embodiments, one reference locus is analyzed together with a target locus. In some embodiments, two reference loci are analyzed together with a target locus. In some embodiments, more than two reference loci are analyzed (e.g., three, four, five, six, or more than six) reference loci are analyzed together with a target locus.

III. Copy Number Determination

Determination of copy number of a target locus typically involves performing a plurality of biological assays on a plurality of specimens as described herein.

1. Biological Specimens

Any of a variety of biological specimens may be suitable for use with methods disclosed herein. Generally, any biological specimen containing nucleic acids (e.g., cells, tissue, etc.) may be used. In certain embodiments, biological specimens contain at least one target locus and at least one reference locus. Types of biological specimens include, but are not limited to, cells, tissue, whole blood, plasma, serum, urine, stool, saliva, cord blood, chorionic villus samples amniotic fluid, and transcervical lavage fluid. Tissue biopsies of any type may also be used. Cell cultures of any of the aforementioned specimens may also be used in according with inventive methods, for example, chorionic villus cultures, amniotic fluid and/or amniocyte cultures, blood cell cultures (e.g., lymphocyte cultures), etc. In some embodiments, biological specimens comprise cancer cells.

In some embodiments, biological specimens are prenatal samples. For example, biological specimens may comprise fetal cells or cell-free nucleic acids. In some embodiments biological specimens may comprise both cell-free fetal nucleic acids and cell-free maternal nucleic acids, e.g., maternal blood, serum or plasma taken from a pregnant woman. For example, a sample such as amniotic fluid and/or maternal blood can be taken from a pregnant woman and can be assayed for copy number of a target locus. Copy number estimates from such samples may provide information relating to the disease status of a fetus which is useful, among other things, in prenatal diagnostic applications.

Biological specimens directly taken from an individual or patient can be used for biological assays. In some cases, one or more procedures can be performed on biological specimens before the specimens are subject to the biological assays. For example, if biological specimens contain a solid and/or semi-solid mass of tissue, the biological specimens can first be processed into single cell suspensions. In some embodiments, if biological specimens comprise fluid and cells, cells can first be separated from fluid. In some embodiments, if biological specimens comprise fluid, the fluid may be fractionated. For example, blood samples may be fractionated into blood components (e.g., plasma and serum) and one or more of the components may be assayed.

In some embodiments, biological specimens are stored for a certain period of time under suitable storage conditions. Specimens may be stored at a temperature or within a temperature range suitable for preserving quality of nucleic acids within the specimens. Such ranges may in some embodiments depend on the specimen type. In some embodiments, suitable storage conditions comprise temperatures ranging between about 37° C. to about −220° C., inclusive. In some embodiments, samples are stored at about 4° C., at about 0° C., at about −10° C., at about −20° C., at about −70° C., or at about −80° C. In some embodiments, samples are stored for more than about twenty-four hours, more than two days, more than three days, more than four days, more than five days, more than six days, more than one week, more than two weeks, more than three weeks, more than four weeks, more than one month, or more than two months. Some (e.g., an aliquot) or all of a previously stored biological specimen may be used during a biological assay.

In some embodiments, one or more molecular biological manipulations may be performed on such biological specimens. Such manipulations can be performed before and/or after storing and include, but are not limited to, tissue homogenization, nucleic acid extraction, protein extraction, treatment to remove ribonucleic acids (e.g., using RNAses), treatment to remove and/or break down proteins (e.g., using proteases), treatment to disrupt cell membranes (e.g., with detergents), isolation of nucleic acids, etc. Such manipulations are known in the art and are described, for example, in Sambrook et al. (1989) "Molecular Cloning: A Laboratory Manual." 2nd Ed., Cold Spring Harbour Laboratory Press: New York, the entire contents of which are herein incorporated by reference.

In some embodiments, cells in biological specimens are counted (i.e., an estimate of the total number of cells in a sample is obtained). Cell counting may facilitate, for example, determining amount of a sample to obtain a certain estimated number of genome equivalents in suitable biological specimen for analysis. In some embodiments, each biological specimen contains nucleic acids from roughly the same number of cells.

In some embodiments, the total amounts of nucleic acids in biological specimens are quantitated before biological specimens are assayed. In some embodiments, the amount of a subset of nucleic acid in a biological specimen (e.g., the amount of fetal nucleic acid in a sample comprising a mixture of fetal and maternal nucleic acid) is quantitated before the biological specimen is assayed. In some embodiments, the total amounts of deoxyribonucleic acids in biological specimens are quantitated before biological specimens are assayed. In some embodiments, each biological specimen contains roughly the same amount of total nucleic acid. In some embodiments, each biological specimen contains roughly the same amount of total deoxyribonucleic acid. In some embodiments, each biological specimen contains roughly the same number of genome equivalents as other biological specimens in a plurality being analyzed.

2. Biological Assays

Typically, one or more biological assays are performed to analyze the copy number of the target locus and reference locus/loci in each biological specimen. Generally, biological assays suitable for this purpose involve assays that generate a detectable signal whose level correlates, directly or indirectly, to copy number of a locus (e.g., a target locus or reference locus) in a biological specimen or sample.

The detectable signal can be generated in any of a variety of ways, for example, using excitable fluorophores, enzymatic products (such as precipitates whose amounts can be measured using spectrophotometers), etc.

In certain embodiments, the level of detectable signal correlates with amount of nucleic acid in a sample, and the amount of nucleic acid in the sample is related to the copy number of a locus (e.g., target locus or reference locus). In some embodiments, detectable signals generated in the biological assay(s) correlate with deoxyribonucleic acids in a sample or biological specimen. In some embodiments, detectable signals generated in the biological assay(s) correlate with the amount of nucleic acid (e.g., deoxyribonucleic acid) in a biological specimen or sample on an approximately linear scale. In some embodiments, detectable signals generated in the biological assay(s) correlate with the amount of nucleic acid (e.g., deoxyribonucleic acid) in a biological specimen or sample on an approximately logarithmic scale. In some embodiments, detectable signals generated in the biological assay(s) correlate exponentially with amount of nucleic acid (e.g., deoxyribonucleic acid) in a sample or biological specimen. In some embodiments, the nature of the correlative relationship between the detectable signal can be determined empirically.

In certain embodiments, detectable signals that are generated are read and/or recorded in real time, so that, for example, it is possible to generate a curve of detectable signal for a biological specimen or sample with respect to time.

For example, in some embodiments, a biological assay suitable for the invention is a real time polymerase chain reaction (rtPCR) method that involves amplification of nucleic acids and quantitation of amount of nucleic acid as it is amplified in real time. Amplification of a particular target or reference locus can be facilitated using appropriate oligonucleotide primers designed to hybridize to nucleic acid sequences flanking and/or within target or reference loci. In some embodiments, the biological assay include a step of detecting signals associated with amplicons from a target locus or reference locus at each amplification cycle.

For example, in a TAQMAN™ (a trademark of Roche Molecular Systems) real-time PCR assay, a quenched fluorescent probe allows quantitation of amplified nucleic acids in real time. (See, e.g., Heid et al. (1996) "Real time quantitative PCR," *Genome Research.* 6:986-994 and Gibson et al. (1996) "A novel method for real time quantitative RT-PCR," *Genome Research.* 6:995-1001, the entire contents of both of which are herein incorporated by reference.) The quenched fluorescent probe typically comprises an oligonucleotide designed to hybridize to a nucleic acid, typically a PCR amplification product of interest (e.g., an amplicon from a target locus or reference locus) conjugated to a fluorophore and to a fluorescent quencher. The fluorescent quencher is normally in proximity to the fluorophore on a given TAQMAN™; therefore, no signal can be detected from the fluorophore. When a TAQMAN™ probe molecule is hybridized to a nucleic acid that is being amplified, the fluorophore can be released from the probe by exonuclease activity of the polymerase during the extension portion of an amplification cycle. Once released from the probe and (thus away from the quencher), a fluorophore can be detected. When excited by the appropriate wavelength, the fluorophore will emit light of a particular wavelength spectrum characteristic of that fluorophore. Detectable signal from the fluorophore can therefore be indicative of amplification product. As fluorescent signal in a sample or biological specimen can be measured in real time, TAQMAN™ real time PCR allows quantitation of amplification product (e.g., amplicon from a target locus or reference locus) in real time, e.g., at each amplification cycle.

Any of a variety of fluorophores may be used, as are methods for conjugating them to probes. (See, for example, R. P. Haugland, "*Molecular Probes: Handbook of Fluorescent Probes and Research Chemicals 1992-1994*", 5$^{th}$ Ed., 1994, Molecular Probes, Inc.). Non-limiting examples of suitable fluorophores include fluorescein, rhodamine, phycobiliproteins, cyanine, coumarin, pyrene, green fluorescent protein, BODIPY®, and their derivatives. Both naturally occurring and synthetic derivatives of fluorophores can be used. Examples of fluorescein derivatives include fluorescein isothiocyanate (FITC), Oregon Green, Tokyo Green, seminapthofluorescein (SNAFL), and carboxynaphthofluorescein. Examples of rhodamine derivatives include rhodamine B, rhodamine 6G, rhodamine 123, tetramethyl rhodamine derivatives TRITC and TAMRA, sulforhodamine 101 (and its sulfonyl chloride form Texas Red), and Rhodamine Red. Phycobiliproteins include phycoerythrin, phycocyanin, allophycocyanin, phycoerythrocyanin, and peridinin chlorophyll protein (PerCP). Types of phycoerythrins include R-phycoerythrin, B-phycoerythrin, and Y-phycoerythrin. Examples of cyanine dyes and their derivatives include Cy2 (cyanine), Cy3 (indocarbocyanine), Cy3.5, Cy5 (indodicarbocyanine), Cy5.5, Cy7, BCy7, and DBCy7. Examples of green fluorescent protein derivatives include enhanced green fluorescent protein (EGFP), blue fluorescent protein (BFP), cyan fluorescent protein (CFP), and yellow fluorescent protein (YFP). BODIPY® dyes (Invitrogen) are named either for the common fluorophore for which they can substitute or for their absorption/emission wavelengths. BODIPY® dyes include BODIPY FL, BODIPY R6G, BODIPY TMR, BODIPY TR, BODIPY 581/591, BODIPY 630/650, and BODIPY 650/665.

Alexa Fluor® dyes (Invitrogen) are also suitable for use in accordance with some embodiments of the invention. Alexa Fluor® dyes are named for the emission wavelengths and include Alexa Fluor 350, Alex Fluor 405, Alexa Fluor 430, Alexa Fluor 488, Alex Fluor 500, Alexa Fluor 514, Alexa Fluor 532, Alexa Fluor 546, Alexa Fluor 555, Alexa Fluor 568, Alexa Fluor 594, Alexa Fluor 610, Alexa Fluor 633, Alexa Fluor 647, Alexa Fluor 660, Alexa Fluor 680, Alexa Fluor 700, and Alexa Fluor 750.

Commercially available fluorophores such as VIC™, JOE™, and HEX™ (each of which are available from Applied Biosystems) may also be used.

In some embodiments, a TAMRA molecule is used as a quencher for a FAM fluorophore.

In some embodiments, two different probes are used, one for the target locus and another for the one or more reference locus/loci. For example, a probe with one type of fluorophore may be used for the target locus, and a probe with another type of fluorophore whose emission spectrum is distinguishable from the other probe is used for the reference locus. In some embodiments, a probe with a FAM fluorophore is used with a probe with a VIC fluorophore.

In PCR amplification, amplification product increases during several phases, typically following a pattern of an exponential phase, followed by a linear phase and then a plateau phase. During the exponential phase, product (e.g., amplicon from a target locus or reference locus) typically doubles during every cycle of PCR because reagents are fresh and available. As reagents are consumed and depleted, reactions begin to slow down during the "linear phase" and the amount of amplicon no longer doubles with each cycle. Finally, as reactions slow even more and stop all together, a "plateau" is reached. Thus, a curve of detectable signal (e.g., fluorescent signal) from a specimen or sample plotted against time will typically show an exponential phase, linear phase, and plateau phase, in that order. In certain embodiments, the number of PCR amplification cycles performed is chosen such that reactions proceed at least through the exponential phase, at least into the linear phase, and/or at least into the plateau phase. For example, typically at least 24, 25, 26, 27, 28, 29, 30, 31, 32, 33, 34, 35, 36, 37, 38, 39, 40, 41, or 42 amplification cycles are performed.

Curves of detectable signal over time can be used to estimate copy number as described herein. A predetermined threshold of signal is chosen, and the number of PCR amplification cycles required to reach a threshold in a given biological specimen or sample is called the cycle threshold (Ct) value. The Ct value for a target locus in a given biological specimen of interest (also referred to as "test sample") can be compared against a Ct reference value typically associated with a known copy number. In some embodiments, the Ct reference value is obtained by analyzing a reference locus with a known copy number (denoted 'Z'); in some such embodiments, a reference locus in the same biological sample as the target locus is analyzed, and values obtained for each are compared against each other as described below.

In certain embodiments, the predetermined threshold of signal is chosen such that all or most samples would be expected to reach the threshold during the exponential part of the PCR amplification reaction. In certain embodiments, determining copy number estimates comprises determining a value ΔCt, defined as the difference between the cycle threshold values between the target gene and that of the one or more reference genes as shown:

$$\Delta Ct = Ct_R - Ct_T \qquad \text{(Equation 1)}$$

wherein $Ct_T$ is the Ct value for the target locus in a given test sample and $Ct_R$ is the Ct reference value, as described above.

Typically, ΔCt is related to the ratio of the copy number (T) of the target locus in the given biological specimen and copy number (Z) of the reference locus (the copy number of which is known). For example, signal representing amplicon for a target locus that is present in one copy per genome will lag behind one cycle of amplification as signal representing amplicon for a reference locus that is present in two copies. Accordingly, the relationship between ΔCt and the ratio of the copy number (T) of the target locus and the copy number (Z) of the reference locus can be defined according to the following equation:

$$-\Delta Ct = \log_2\left(\frac{Z}{T}\right) \qquad \text{(Equation 2)}$$

wherein ΔCt and Z are defined as above and wherein T is the number of copies of the target locus in the biological specimen being analyzed. Thus, T can be determined from Z and ΔCt according to the following equation:

$$T = Z \cdot 2^{\Delta Ct} \qquad \text{(Equation 3)}$$

For example, when Z=2 and ΔCt=−1, then, T=1, which is consistent with the understanding that signal representing amplicon for a target locus with one copy per genome will lag behind one cycle when compared to the signal representing amplicon for a reference locus with two copies per genome.

As another example, when Z=4 and ΔCt=−1, then T=2.

In some embodiments, T is estimated to be an integer value.

In some embodiments, T is estimated to be a non-integer value. It may be possible to obtain a non-integer estimation for T, for example, from heterogeneous biological samples. Examples of heterogeneous biological specimens that may give rise to non-integer T estimates include, but are not limited to, populations of polyclonal cancer cells having heterogeneous copy numbers of a target locus and samples containing both maternal and fetal nucleic acids.

Although real-time PCR methods have been used for illustrative purposes, other biological methods that are used to quantitate (directly or indirectly) gene copy number can be adapted for use with inventive methods herein. Such methods include, but are not limited to, PCR-ELOSA (PCR-enzyme-linked oligosorbent assays; also known as "PCR-ELISA"), array-based comparative genomic hybridization (aCGH), and high-throughput sequencing (e.g., quantitative next generation sequencing methods). In PCR-ELOSA assays, PCR products are hybridized to an immobilized capture probe as amplification proceeds. PCR-ELOSA is sometimes used as an alternative to real-time PCR. In aCGH (also known as matrix CGH), a cDNA microarray is used in which each spot on the array contains a genomic target. In high-throughput sequencing, parallel sequencing reactions using multiple templates and multiple primers allows rapid sequencing of genomes or large portions of genomes.

In some embodiments, in addition to performing biological assays to determine copy number, other assays are performed that may provide additional useful information. For example, the target locus in a biological specimen may be sequenced to determine if there are any mutations that contributed to lower copy numbers of a target locus.

3. Assay Formats and Controls

In certain embodiments, a plurality of biological assays are conducted in parallel to facilitate more reliable and accurate copy number estimates and statistical analysis. Typically, multiple biological specimens or samples obtained from multiple individuals are assayed in parallel. In some embodiments, the plurality of biological assays (which in certain embodiments comprises assays on specimens from different individuals) also include replicate assays conducted for a particular individual or on a particular biological specimen or sample. For example, multiple specimens may be obtained from a particular individual, and/or a single specimen from a particular individual may be divided into sub-units (each sub-unit being used as a replicate or stored for later use) for replicate assays. The number of replicates used may be chosen depending on pre-determined statistical thresholds or empirically. In some embodiments, duplicates, triplicates, quadruplicates, pentuplicates, sextuplicates, septuplicates, octuplicates, nonuplicates, decuplicates, or more than 10 replicates are used. In some embodiments, quadruplicates are used.

Using replicates facilitates making certain statistical determinations, as explained further below. For example, in some embodiments, the statistical confidence of the copy number call is determined by the calculation of a measurement confidence for replicate biological assays and a call confidence based on the plurality of copy number estimates.

In some embodiments, control samples are analyzed in parallel with biological specimens obtained from individuals or patients (test samples). Control samples may include, but are not limited to, no template controls (for example, in amplification-based methods), biological samples having known (e.g., predetermined) copy numbers of the target locus, other reference samples used to calibrate detectable signals, and any combination thereof. Control samples having known copy numbers can be obtained from a number of sources including, but not limited to, verified cell lines and/or biological specimens from normal individuals or patients confirmed to have diseases associated with abnormal copy numbers of a target locus (e.g., SMA patients confirmed to have missing exon 7 of SMN1). Typically, replicate assays are conducted on the controls, as described above for test samples. In some embodiments, duplicates of controls are used.

In some embodiments, the plurality of biological assays (e.g., from different individuals) can be conducted in an array format. A variety of array formats can be used to facilitate assaying multiple biological specimens. In some embodiments, the plurality of biological assays can be conducted on a multi-well plate. Exemplary multi-well plates suitable for the invention include, but are not limited to, 24-well, 48-well, 96-well and 384-well plates. Such plates may be made of optically clear materials suitable for use with methods that involve detecting signals. Multiples of such plates can be used. Typically, each biological sample or a portion or sub-unit thereof is placed in an individual well of such a plate, and a plate may contain one or more empty wells or wells filled only with solution (e.g., buffer). In some embodiments, each plate contains a certain number and type of controls, as explained above. For example, a no template control and controls with known copy numbers may be included on each plate. As a non-limiting example, a 384-well plate may contain quadruplicates of 96 different biological specimens or controls.

FIG. 2 depicts an exemplary multi-well plate containing wells that hold controls and sample replicates.

Additionally or alternatively, a suitable assay format facilitate conducting at least 50, 100, 120, 140, 160, 180, 200, 220, 240, 260, 280, 300, 320, 340, 360, 380, 400, 420, 440, 460, 480, 500, 520, 540, 560, 580, 600, 620, 640, 660, 680, 700, 720, 740, 760, 780, 800, 820, 840, 860, 880, 900, 920, 940, 960, 980 or 1000 biological assays simultaneously.

Typically, a majority of the plurality of biological specimens present on a multi-well plate (or other forms of array) contain normal copy numbers of a target locus. In some embodiments, more than 75%, 80%, 85%, 90%, 91%, 92%, 93%, 94%, 95%, 96%, 97%, 98%, or 99% of the samples present on a multi-well plate contain normal copy numbers of a target locus. In some embodiments, more than 99.0%, 99.1%, 99.2%, 99.3%, 99.4%, 99.5%, 99.6%, 99.7%, 99.8%, or 99.9% of the samples present on a multi-well plate contain normal copy numbers of a target locus.

IV. Assessing Quality of Copy Number Estimates and Statistical Confidence

Inventive methods according to the invention include a step of assessing quality of copy number estimates and/or statistical confidence of copy number calls, thereby determining if a copy number call can be made for a target locus in a biological specimen. In some embodiments, assessing quality of copy number estimates and/or statistical confidence is carried out on a computing module executing an algorithm, as described in the "Systems" section herein.

In some embodiments involving multi-well plates, an algorithm records wells in which certain quality control metrics fail, and which metrics had failed. In some embodiments, an algorithm records results from statistical tests and/or status of a sample with respect to that test (e.g., passing or failing according to predetermined thresholds or ranges).

1. Calibrated Copy Number Estimates

In embodiments in which a plurality of biological assays are conducted on a plurality of biological specimens (e.g., from different individuals) in parallel, ΔCt values (see Equation 1) can be calculated for each specimen. For illustration purposes only, a multi-well plate is used as an example. However, methods described herein can be used for any assay format.

In some embodiments, a "calibrator" value ($\Delta \overline{C}t$) for all the samples the plate is calculated to determine the background cycle number difference between a target locus with normal copy number and the one or more reference loci. Typically, the calibrator is calculated based on a trimmed mean of the ΔCt values from all the biological assays on the plate. In some embodiments, an 80% trimmed mean is used:

$$\Delta \overline{C}t = \text{trimmean}(\Delta Ct, 80\%) \quad \text{(Equation 4)}$$

Based on the calibrator, copy number estimate for the target locus ($T_{Ci}$) can be derived for each sample on the plate (e.g., calibrated or normalized copy number estimate). In some embodiments, normalized $T_{Ci}$ can be obtained on a linear scale according to the following:

$$(\text{Linear scale}) \quad T_{Ci} = Z \cdot 2^{(\Delta Ct - \Delta \overline{C}t)} \quad \text{(Equation 5)}$$

In some embodiments, normalized $T_{Ci}$ can be obtained on a log-scale according to the following:

$$(\text{Log scale}) \quad T_{Ci} = Z + \Delta Ct - \Delta \overline{C}t, \quad \text{(Equation 6)}$$

Copy number estimates based on the replicate assays for a same individual or for same biological specimen can be averaged. In some embodiments, a copy number call can be made by rounding off the average copy number estimates.

2. Quality Control Metrics

In certain embodiments, a suite of quality control metrics is performed in order to evaluate whether a copy number call can be made for the target locus in each biological specimen. In some embodiments, quality of copy number estimates for the target locus is assessed based at least in part on the quality of data generated for the one or more reference loci, as discussed herein.

Cycle Number Check

In some embodiments, the suite of quality control metrics includes a cycle number check. If the Ct value for the one or more reference loci for a given biological specimen is outside a predetermined range, the specimen fails the cycle number check. In some embodiments, the predetermined range comprises a predetermined upper limit Ct value. In such embodiments, if the Ct value for one or more of the reference loci for a particular biological specimen exceeds the predetermined upper limit Ct value, then the Ct measurement fails the cycle number check. In some embodiments, the predetermined upper limit Ct value is specified in a configuration file. In some embodiments, the predetermined upper limit Ct value is greater than 30, 31, 32, 33, 34, 35, 36, 37, 38, 39, 40, 41, 42, 43, 44, 45, 46, 47, 48, 49, or 50 cycles.

Slope of Signal Level Curve

In some embodiments, the suite of quality control metrics includes a slope check—a verification that the slope of signal level (e.g., fluorescence level from a curve of an amplification reaction) for the one or more reference loci in each biological specimen is within a predetermined range. If the slope for a particular biological specimen does not fall within the predetermined range, the specimen fails the slope check. In some embodiments, a slope S is calculated for the three cycle measurements closest to the Ct measurement. For example, $Y_2$ can be taken as the log-transformed signal level (normalized to background) for the cycle closest to the Ct value. $Y_1$ and $Y_3$ (both of which are also normalized to background) can be taken as the log-transformed signal levels for the cycle just before and just after, respectively, the cycle closest to the Ct value. In some embodiments, the fluorescent value is based on a log 10 scale. Thus, in some embodiments, the slope is calculated according to:

$$S = \frac{Y_3 - Y_1}{2} \quad \text{(Equation 7)}$$

In some embodiments, the predetermined range of acceptable values for S is specified in a configuration file. In some embodiments, an acceptable range for S is between about 0.15 and 0.55.

Sample Coefficient of Variation

In some embodiments in which specimen replicates are used (as discussed above in "assay formats"), the sample coefficient of variation (sample CV) between replicates is calculated. The sample CV for a biological specimen must be lower than a predetermined threshold, for the CV check to pass for that specimen. The sample CV is calculated on a linear scale and is the ratio of the sample standard deviation and the sample mean between all the replicates of a biological specimen. Sample CV for a zero copy number sample is calculated as the ratio of the standard deviation and the mean plus one. If the sample CV exceeds the predetermined threshold, then a copy number call is not made for that biological specimen. In some embodiments, the predetermined threshold for the sample CV is specified in a configuration file. In some embodiments, the predetermined threshold for the sample CV is 0.15.

3. Statistical Analyses

In certain embodiments, one or more statistical analyses are performed to help determine if a copy number call can be made for a biological specimen. In some embodiments, a statistical confidence is assessed by determining a measurement confidence and/or a call confidence, as described below.

Measurement Confidence

In some embodiments in which sample replicates are used, a measurement confidence value is determined. If the measurement confidence falls below a predetermined threshold, values (e.g., copy number estimate) obtained for a specimen fail the measurement confidence check and a copy number call cannot be made. Measurement confidence is an indicator of intra-sample variability and examines the mean and the variability around the mean. Measurement confidence is calculated as the largest normal confidence interval around the mean copy number estimate for a specimen or sample (averaged across replicates) that would fit within predetermined copy number limits for a particular copy number. In some embodiments, an assumption of normality of the average across all replicates of a sample is made. For a normal distribution, the mean is the average copy number estimate across all replicates on the linear scale, and the standard deviation is the standard error of the mean (standard deviation divided by the square root of the number of replicates). In some embodiments, copy number limits are specified in a configuration file. Examples of copy number call limits are shown in Table 2.

TABLE 2 exemplary copy number limits

| Copy number | Lower limits | Upper limits |
|---|---|---|
| 0 | Negative of upper limit | 0.01, 0.1 |
| 1 | 0.5, 0.6 | 1.4, 1.45 |
| 2 | 1.6, 1.65 | 2.35, 2.4 |
| 3 | 2.4, 2.5 | 3.4, 3.5 |

Call Confidence

In some embodiments, a call confidence is calculated for each specimen. In some embodiments, if the call confidence for a given specimen is less than a predetermined threshold, a determination is made that the copy number call for the target locus can not be made. In some embodiments, the predetermined threshold is specified in a configuration file.

Background Variability

In order to calculate call confidence, background variability is first calculated as the variance of call estimates for samples having Z copies of the target locus (wherein Z is the known normal number of copies of the reference locus). A predetermined critical number of specimens having Z copies of the target locus (Z-copy specimens) are required for calculating this background variability; the predetermined number may be specified in a configuration file. In some embodiments, the predetermined critical number is 20.

In certain embodiments, specimens must pass certain requirements in order to be included in the background variability calculation.

In some embodiments, the requirements include at least one or any combination of: a) passing quality control metrics (Ct value for reference locus within a predetermined range, slope of signal level for reference locus within a predetermined range, measurement confidence meeting a predetermined threshold, and sample CV lower than a predetermined threshold for); b) not being a control specimen; c) estimated to have roughly Z copies of the target locus; and d) being of a particular predetermined sample type (e.g., blood). In some embodiments, the requirement d) (the requirement of being of a particular predetermined sample type) is forgone if the number samples of the predetermined sample type falls below the predetermined critical number of Z-copy specimens.

In some embodiments, the requirements include both passing quality control and statistical confidence metrics as outlined in a) above and having an copy number estimate equal to Z for the target locus.

Sample Type Adjustment

In some embodiments, the background variability is adjusted to account for different variabilities associated with sample type. Typically, no sample adjustment is made if requirement d) is removed. An adjustment can be made for each sample type; i.e., an adjustment value can be subtracted or added. In some embodiments, no sample adjustment is made for most samples. In some embodiments, background variability for amniotic fluid and/or amniotic cell cultures samples are adjusted by 0.03 units. In some embodiments, background variability for chorionic villus samples are adjusted by 0.03 units.

Call Confidence

Having obtained a background variability that may or may not be adjusted for sample type, a call confidence value can be determined. The call confidence can be based on a plurality of copy number estimates. A predetermined critical number of specimens having Z copies of the target locus (Z-copy specimens) are required for calculating call confidence; the predetermined number may be specified in a configuration file. In some embodiments, the predetermined critical number is 20.

In some embodiments, algorithms used to determine call confidence assume that copy number estimates are normally distributed and have equal variances across copy numbers. Any statistical test that assumes normal distribution can be used. In some embodiments, a Student's t-test is used to determine p-values for each specimen.

In some embodiments, the hypothesis that is tested in the statistical test is that the observed copy number estimate for the specimen is actually obtained from adjacent copy number distributions. That is, if the copy number estimate is two, the algorithm determines the probabilities that the sample actually has one or three copies. The algorithm sums the p-values from each of the two tests (in this example, for the one-copy hypothesis and the three-copy hypothesis). Confidence is calculated by subtracting the sum of the p-values from 1.

If the copy number estimate is zero (or at the maximum possible copy number, if there is one), there is only one adjacent copy number distribution, the distribution for one copy (or the maximum minus one). In such a case, the algorithm uses the single p-value obtained from testing the hypothesis that the copy number estimate is obtained from the adjacent copy number distribution. Call confidence is calculated by subtracting that p-value from 1.

In some embodiments, call confidence statistic is calculated on the log scale of the copy number estimates. The copy number t-distribution means are determined by averaging all of the copy number estimates for the particular copy number. If there are no estimates for a particular gene copy category, the means are assumed to be −2, 1, 2, and 2.585.

Call confidence QC test is performed for each sample. If the call confidence is less than the threshold specified in the configuration file, the sample fails the call confidence QC metric.

4. Plate Quality Control Metrics

In certain embodiments in which a plurality of biological specimens in a plate is analyzed, a plate alert is generated if certain quality control metrics from the plate fail. For example, in some embodiments, every control sample in a plate except for blank controls is checked for quality control metrics and/or are analyzed statistically as described above (e.g., Ct value check, slope check, measurement confidence, call confidence, and sample CV). If any of these quality control metrics are failed for a control sample on a plate, a plate alert is generated with a list of failed wells within the plate and the failed metrics. Samples serving as controls for copy numbers are also checked for correspondence with expected copy numbers. For example, in some embodiments, a plate is failed if any of the one or more control samples fails one of the quality control or statistical confidence assessments or if an estimate for any individual control sample does not equal the predetermined or expected copy numbers. In some embodiments, a plate is failed if the number of Z-copy (wherein Z is the number of copies of the reference locus, e.g., 2 in some embodiments) samples is below a predetermined threshold and/or is insufficient for estimation of t-distribution parameters for the call confidence statistic. In some embodiments, a plate is failed if the confidence interval around the average of the Z-copy samples is outside of predetermined limits. In some embodiments, a plate is failed if the standard deviation of the copy number estimates for Z-copy samples is above a predetermined threshold.

In some embodiments, a computing module finds controls by well location based on a predetermined plate layout.

V. Systems or Computer Readable Mediums

In some embodiments, inventive methods described herein can be implemented on systems or computer readable mediums such as those systems and mediums described herein. Execution of inventive methods by the systems and media described herein can determine copy number estimates for a target locus and assessing quality of the copy number estimates and/or statistical confidence of the copy number call, and alerting to a user whether a copy number call can be made for the target locus. In some embodiments, the systems and media described herein can also indicate whether an individual has a disease, disorder, or condition associated with abnormal copy number of a target locus or a carrier thereof.

Systems provided herein can, in some embodiments, be described as functional modules, clients, agents, programs, executable instructions or instructions included on a computer readable medium such that a processor can execute the instructions to perform a method or process (e.g., calculation of copy number estimates and/or statistical analysis). The functional modules described herein need not correspond to discreet blocks of code. Rather, functional portions of the functional modules can be carried out by the execution of various code portions stored on various media and executed at various times. Furthermore, it should be appreciated that the modules may perform other functions, thus the modules are not limited to having any particular functions or set of functions. In some embodiments, these functional modules can be executed by a computing device. The functional modules can be stored on the computing device, or in some embodiments can be stored on an external storage repository or remote computing machine.

Figure 3A:
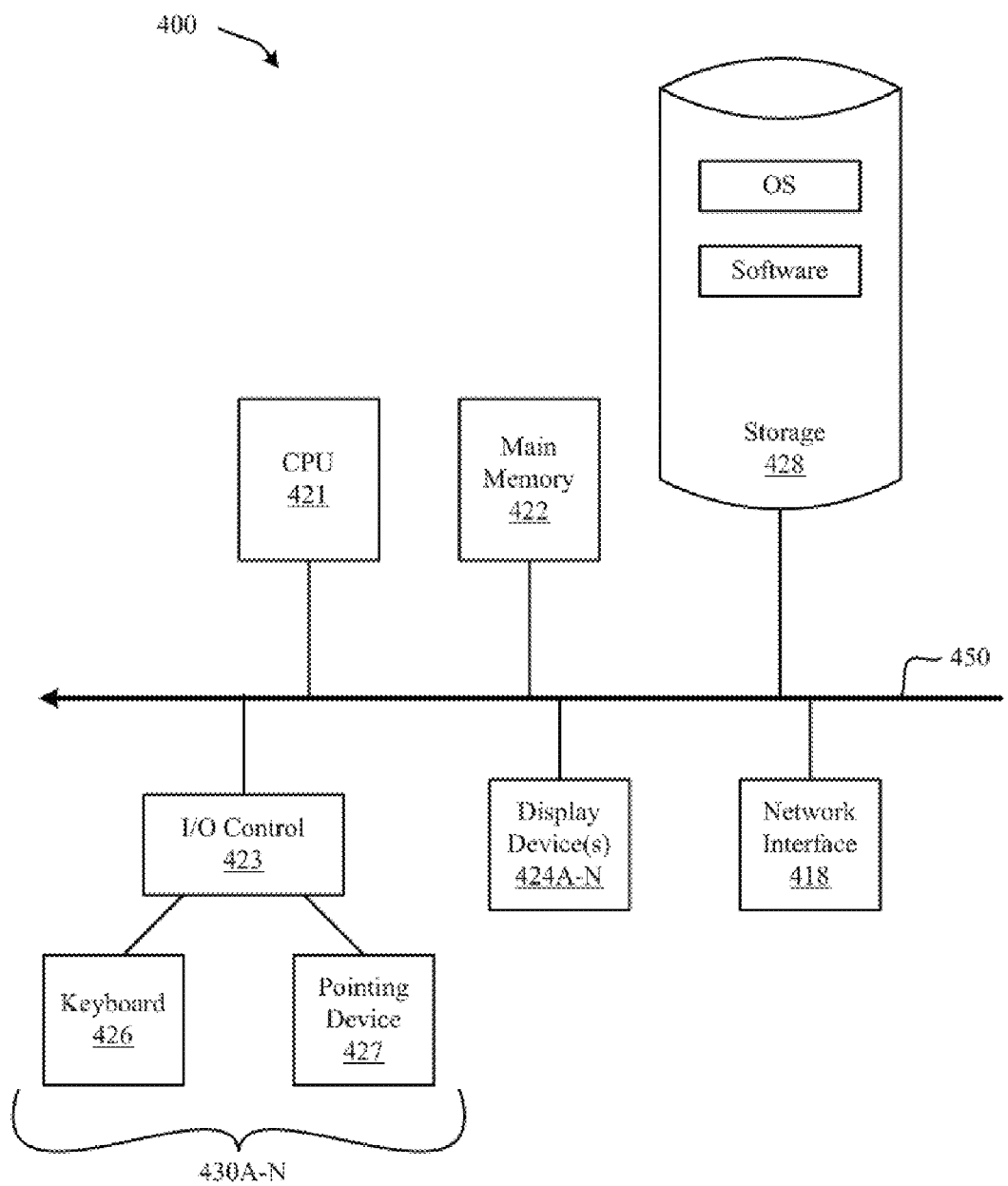
FIGS. 3A and 3B are block diagrams that illustrate an embodiment of a computing device that can be included in an analysis system.

Illustrated in FIG. 3A is one embodiment of a computing device 400 that can store and/or execute the above-described function modules. The computing device, in some embodiments, can be a computer, computing machine or any other device having a processor and a memory. In some embodiments, the computing device can be a virtual machine managed by a hypervisor installed on a physical computing machine. Included within the computing device 400 is a system bus 450 that communicates with the following components: a central processing unit 421; a main memory 422; storage memory 428; an input/output (I/O) controller 423; display devices 424A-424N; and a network interface 418. In one embodiment, the storage memory 428 includes an operating system and software routines both of which can be executed by the processor 421. The I/O controller 423, in some embodiments, is further connected to a key board 426, a pointing device 427 and any other input device. Other embodiments may include an I/O controller 423 connected to more than one input/output device 430A-430N.

Figure 3B:
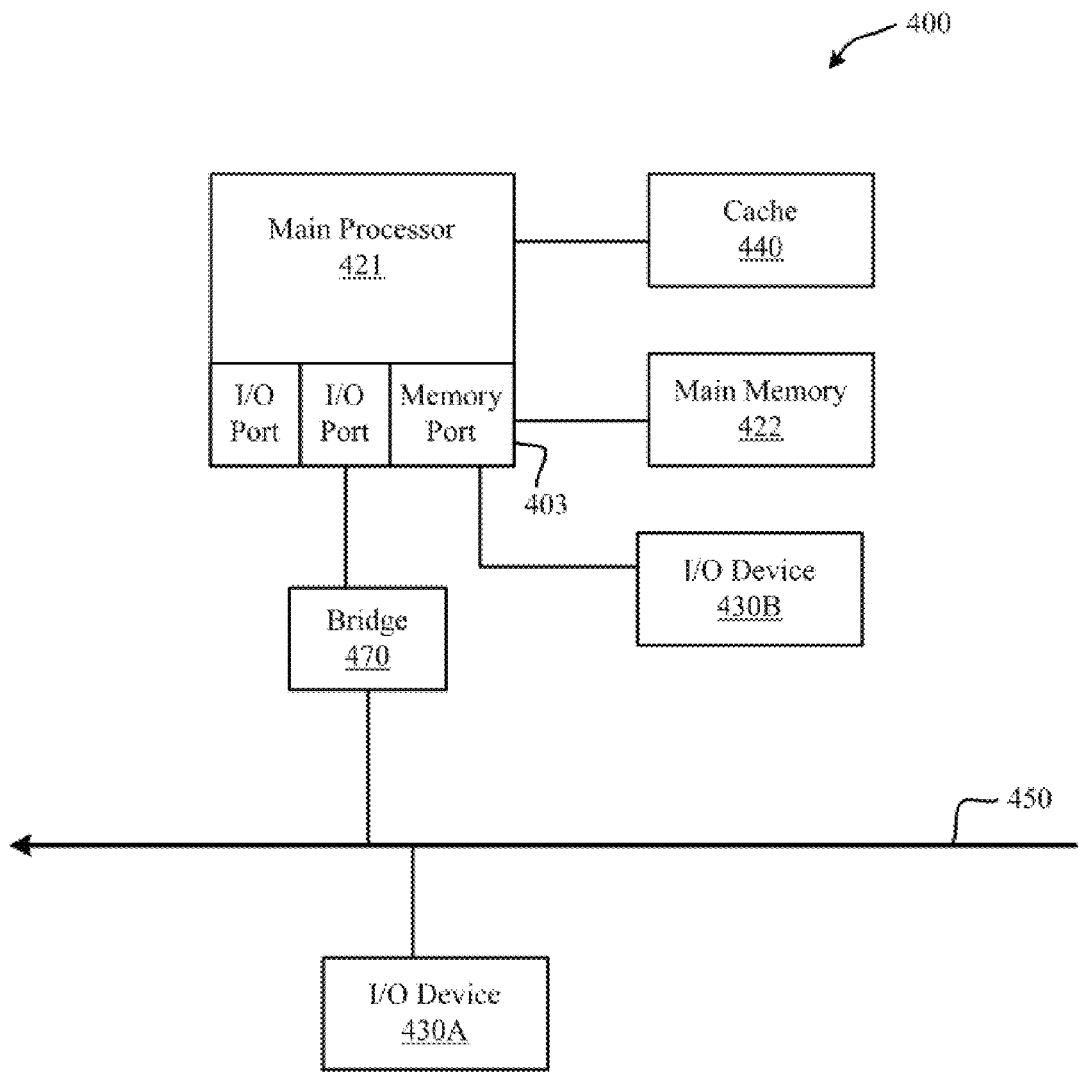

FIG. 3B illustrates another embodiment of a computing device 400 that can store and/or execute the functional modules described herein. In some embodiments, the computing device 400 includes a system bus 450 that can communicate with the following components: a bridge 470, and a first I/O device 430A. In another embodiment, the bridge 470 further communicates with the main central processing unit 421 that communicates with a second I/O device 430B, a main memory 422, and a cache memory 440. In some embodiments, the central processing unit 421 is further coupled to I/O ports and a memory port 403.

Embodiments of the computing machine 400 can include a central processing unit 421 characterized by any one of the following component configurations: logic circuits that respond to and process instructions fetched from the main memory unit 422. The central processing unit 421, in some embodiments, can include a microprocessor unit, such as: those manufactured by Intel Corporation; those manufactured by Motorola Corporation; those manufactured by Transmeta Corporation of Santa Clara, Calif.; the RS/6000 processor such as those manufactured by International Business Machines; a processor such as those manufactured by Advanced Micro Devices; or any other combination of logic circuits. In still other embodiments, the central processing unit 421 includes any combination of the following: a microprocessor, a microcontroller, a central processing unit with a single processing core, a central processing unit with two processing cores, or a central processing unit with more than one processing core.

In one embodiment, the central processing unit 421 communicates with cache memory 440 via a secondary bus also known as a backside bus, while in another embodiment the processor 421 communicates with cache memory via the system bus 450. The local system bus 450 can, in some embodiments, also be used by the central processing unit 421 to communicate with more than one type of I/O device 430A-430N.

The computing device 400, in some embodiments, includes a main memory unit 422 and cache memory 440. The cache memory 440 and the main memory unit 422, in some embodiments, can be any one of the following types of memory: Static random access memory (SRAM), Burst SRAM or SynchBurst SRAM (BSRAM); Dynamic random access memory (DRAM); Fast Page Mode DRAM (FPM DRAM); Enhanced DRAM (EDRAM), Extended Data Output RAM (EDO RAM); Extended Data Output DRAM (EDO DRAM); Burst Extended Data Output DRAM (BEDO DRAM); Enhanced DRAM (EDRAM); synchronous DRAM (SDRAM); JEDEC SRAM; PC100 SDRAM; Double Data Rate SDRAM (DDR SDRAM); Enhanced SDRAM (ESDRAM); SyncLink DRAM (SLDRAM); Direct Rambus DRAM (DRDRAM); Ferroelectric RAM (FRAM); or any other type of memory. Further embodiments include a central processing unit 421 that can access the main memory 422 via: a system bus 450; a memory port 403; or any other connection, bus or port that allows the processor 421 to access memory 422.

Computer readable media can be stored in the main memory unit 422 and executed by the processor 421. This computer readable media can, in some embodiments, include software programs and any other executable set of instructions that, when executed, instruct the computer to perform one or more functions. This computer readable media can include instructions written in any language, and in some embodiments, in any one of the following languages: Java, J#; Visual Basic; C; C#; C++; Fortran; Pascal; Eiffel, Basic; COBOL; and assembly language.

In some embodiments, the computer readable media can include instructions for carrying out basic computational biology methods known to those of ordinary skill in the art. In particular, the computer readable media can include instructions for carrying out any methods described in the following resources: Setubal and Meidanis et al., *Introduction to Computational Biology Methods* (PWS Publishing Company, Boston, 1997); Salzberg, Searles, Kasif, (Ed.), *Computational Methods in Molecular Biology*, (Elsevier, Amsterdam, 1998); Rashidi and Buehler, *Bioinformatics Basics: Application in Biological Science and Medicine* (CRC Press, London, 2000); and Ouelette and Bzevanis *Bioinformatics: A Practical Guide for Analysis of Gene and Proteins* (Wiley & Sons, Inc., $2^{nd}$ ed., 2001).

In some embodiments, the computing device 400 includes a storage device 428 that can be one or more hard disk drives, one or more redundant arrays of independent disks, or an external storage or media device that can communicate with the computing device 400 via a USB, or serial port. In still other embodiment, the storage device 428 can be a remote storage device that can be accessed using any of the following connections and/or protocols: USB; serial; parallel; Ethernet; Bluetooth; WiFi; Zigbee; Wireless USB; IEEE 802.15; RS-232; RS-484; IEEE 802.3; and IEEE 802.11.

The computing device 400 may further include a network interface 418 to interface to a network such as a Local Area Network (LAN) or Wide Area Network (WAN) via any of the following connections: standard telephone lines, LAN or WAN links (e.g., 802.11, T1, T3, 56 kb, X.25, SNA, DECNET), broadband connections (e.g., ISDN, Frame Relay, ATM, Gigabit Ethernet, Ethernet-over-SONET), wireless connections, or any combination of the above-listed connections. Connections can also be established using a variety of communication protocols (e.g., TCP/IP, IPX, SPX, NetBIOS, Ethernet, ARCNET, SONET, SDH, Fiber Distributed Data Interface (FDDI), RS232, RS485, IEEE 802.11, IEEE 802.11a, IEEE 802.11b, IEEE 802.11g, CDMA, GSM, WiMax and direct asynchronous connections.) In some embodiments, the computing device 400 communicates with additional computing devices, appliances, input devices, storage devices or machines via the network interface 418. This communication can, in some embodiments, be established via any type and/or form of gateway or tunneling protocol such as Secure Socket Layer (SSL) or Transport Layer Security (TLS), Remote Desktop Protocol (RDP) or the ICA protocol. Versions of the network interface 418 can comprise any one of: a built-in network adapter; a network interface card; a PCMCIA network card; a card bus network adapter; a wireless network adapter; a USB network adapter; a modem; multiple network cards; or any other device suitable for interfacing the computing device 400 to a network.

The I/O devices 430A-430N, in some embodiments, can be any of the following devices: a keyboard 426; a pointing device 427; a mouse; a trackpad; an optical pen; trackballs; microphones; drawing tablets; video displays; speakers; inkjet printers; laser printers; and dye-sublimation printers; a USB Flash Drive; or any other input/output device able to perform the methods and systems described herein. An I/O controller 423 may in some embodiments connect to multiple I/O devices 430A-430N to control the one or more I/O devices. In other embodiments, an I/O device 430A-430N can store results, display results or act as a bridge between the system bus 450 and an external communication bus, such as:

a USB bus; an Apple Desktop Bus; an RS-232 serial connection; a SCSI bus; a FireWire bus; a FireWire 800 bus; an Ethernet bus; an AppleTalk bus; a Gigabit Ethernet bus; an Asynchronous Transfer Mode bus; a HIPPI bus; a Super HIPPI bus; a SerialPlus bus; a SCI/LAMP bus; a FibreChannel bus; or a Serial Attached small computer system interface bus.

In some embodiments, the computing machine 400 can connect to multiple display devices 424A-424N, in other embodiments the computing device 400 can connect to a single display device 424, while in still other embodiments the computing device 400 connects to display devices 424A-424N that are the same type or form of display, or to display devices that are different types or forms. Embodiments of the display devices 424A-424N can be supported and enabled by the following: one or multiple I/O devices 430A-430N; the I/O controller 423; a combination of I/O device(s) 430A-430N and the I/O controller 423; any combination of hardware and software able to support a display device 424A-424N; any type and/or form of video adapter, video card, driver, and/or library to interface, communicate, connect or otherwise use the display devices 424A-424N. The computing device 400 may in some embodiments be configured to use one or multiple display devices 424A-424N, these configurations can include: having multiple connectors to interface to multiple display devices 424A-424N; having multiple video adapters, with each video adapter connected to one or more of the display devices 424A-424N; having an operating system configured to support multiple displays 424A-424N; using circuits and software included within the computing device 400 to connect to and use multiple display devices 424A-424N; and executing software on the main computing device 400 and multiple secondary computing devices to enable the main computing device 400 to use a secondary computing device's display as a display device 424A-424N for the main computing device 400. Still other embodiments of the computing device 400 may include multiple display devices 424A-424N provided by multiple secondary computing devices and connected to the main computing device 400 via a network.

In some embodiments, the computing machine 400 can execute any operating system, while in other embodiments the computing machine 400 can execute any of the following operating systems: versions of the MICROSOFT WINDOWS operating systems; the different releases of the Unix and Linux operating systems; any version of the MAC OS manufactured by Apple Computer; and any embedded operating system. In still another embodiment, the computing machine 400 can execute multiple operating systems.

The computing machine 400 can be embodied in any one of the following computing devices: a computing workstation; a desktop computer; a laptop or notebook computer; a server; a handheld computer; a mobile telephone; a portable telecommunication device; a media playing device; a gaming system; a mobile computing device; a notebook; a device of the IPOD family of devices manufactured by Apple Computer; or any other type and/or form of computing, telecommunications or media device that is capable of communication and that has sufficient processor power and memory capacity to perform the methods and systems described herein The functional modules described herein need not correspond to discreet blocks of code. Rather, functional portions of the functional modules can be carried out by the execution of various code portions stored on various media and executed at various times. Furthermore, it should be appreciated that the modules may perform other functions, thus the modules are not limited to having any particular functions or set of functions.

Figure 4:
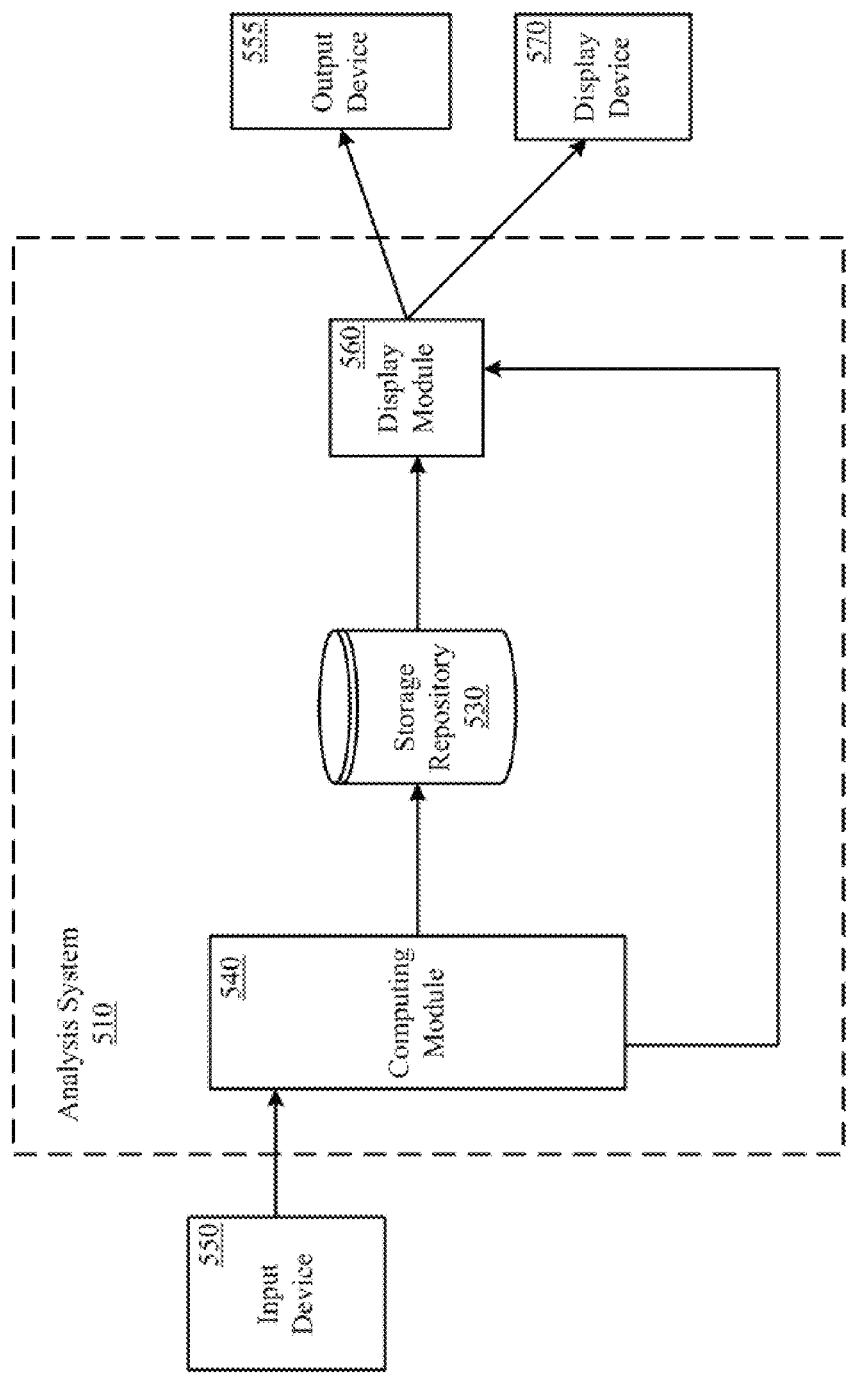
FIG. 4 is a block diagram that illustrates an embodiment of an analysis system.

Illustrated in FIG. 4 is one embodiment of a system 510 that inputs data obtained from biological assays, one or more configuration files, and/or stored reference data (e.g., predetermined threshold limits, control and reference copy numbers, etc) and analyzes the data using any functional module described herein. In one embodiment, an input device 550 can communicate with the analysis system 510, and more specifically with a computing module 540 executing on a processor within the analysis system 510. The computing module 540 can perform any number of functions or methods to obtain and generate information associated with the output data obtained from the input device 550. In some embodiments the computing module 540 can store generated information or obtain data stored in a storage repository 530 included within the analysis system 510. In some embodiments, the computing module 540 can forward report data and other values to a display module 560 within the analysis system 510. In other embodiments, the display module 560 can retrieve report data content from the storage repository 530. The display module 560 communicates with an output device 555 and a display device 570, both of which can display the report data and other information received by the display module 560.

Further referring to FIG. 4, and in more detail, in one embodiment the analysis system 510 can comprise functional modules such as a computing module 540 and a display module 560. In other embodiments, the analysis system 510 can include modules that carry out basic computational biology methods. The analysis system 510, in some embodiments, can be implemented on a single computing device 100. In other embodiments, the analysis system 510 can include one or more computing devices 100. Each computing device 100 included within the analysis system 510 can communicate with the other computing devices 100 included within the system 510. For example, the computing module 540 can be executed by a first computer, while the storage repository 530 and the display module 560 can be implemented by a second computer. In another example, the storage repository 530 can reside on a first computer, while each of the functional modules can be executed by a second computer.

Communication between multiple computers 100 included in the system 510 can, in some embodiments, be facilitated by a network or a direct connection. In other embodiments, the direct connection can include an Ethernet connection, a serial connection or a parallel connection. The network can include any number of sub-networks, and can be a local-area network (LAN), or a wide area network (WAN). Further, the network can include any combination of private and public networks. In one embodiment the network can be any of the networks described herein and the modules and computers included within the analysis system 510 as well as the devices that communicate with the analysis system, can communicate via any of the networks described herein and using any of the network protocols described herein.

In some embodiments, an input device 550 can communicate with the analysis system 510. In other embodiments the input device 550 can communicate directly with a computing module 540 or other modules within the analysis system 510. While FIG. 4 illustrates an input device 550 located outside of the analysis system 510, in some embodiments the analysis system 510 can include the input device 550.

The input device 550 can, in some embodiments, be any device, machine or computer able to output data obtained from a polymerase chain reaction (PCR) assay (in particular, real-time PCR). In other embodiments, the input device 550 can be any device, machine or computer able to output data obtained from any of the assays described herein. The input device 550, in other embodiments, can be a machine or device adapted for performing suitable biological assays that analyze a target locus and one or more reference loci in one or more biological specimens. In some embodiments, the input device 550 reads signal from a TAQMAN probe developed by Applied Biosystems. The input device 550, in some embodiments, measures the amount of fluorescence emitted by fluorophore during degradation of a TAQ probe. The fluorescence amounts can be used to determine an amount of DNA and in some embodiments can determine the number of cycles required to reach a particular level of fluorescence. In some embodiments, the level of fluorescence or the level of fluorescence signals for the target and reference loci can be detected at each amplification cycle. The input device 550 can generate output data representative of the fluorescence signals generated and analyzed during the assay.

In one embodiment, the input device 550 can output a file, array or string of data values that represent the output from an assay. This output file can include one or more characters, numbers or letters that can represent any of the following: level of fluorescence signals; an identifier that identifies a well on a plate; an identifier that identifies a sample or specimen on a plate; a patient; the method by which the sample or specimen was obtained; and any other identifier or information associated with the output. In one embodiment, the input device 550 outputs a flat file where the fluorescence signal data for each sample or specimen is reflected in a group of data comprising a numerical representation of the signal, an identifier identifying the patient, the method used to obtain the sample, the well within which the sample or specimen was placed, and any other similar information. Each group of data, in this embodiment, can be separated by a delimiter such as a parallel line ("|"), a comma, a space or any other character. Each character delimited section of the file can include the fluorescence measurements for specimens included on the plate. In some embodiments, each character delimited section can include the fluorescence measurements for at least two channels in the multi-well plate (e.g., 384-well plate) at each cycle.

In some embodiments, the analysis system 510 can include a driver or other program (Not Shown) that interfaces with the input device 550 to obtain data from the input device. In some embodiments, the driver or program receives raw data from an input device or machine 550, and converts the raw data into a format able to be processed by the programs and modules executing within the analysis system 510. Formatting the information obtained from the input device 550 can include changing the data type, removing extraneous characters, or generating charts, graphs, or other visual representations of the information outputted by the input device 550.

In one embodiment, the computing module 540 can communicate directly with the input device 550 to receive output data from the input device 550. The computing module 540, in some embodiments, can communicate with any of the modules, machines or devices included in the analysis system 510. In other embodiments, the computing module 540 can communicate with the storage repository 530 to store information obtained by the input device 550. In other embodiments, the computing module 540 can communicate with the storage repository 530 to store information generated by the computing module 540. In still other embodiments, the computing module 540 can retrieve information from the storage repository 530 such as calibration information, threshold information and control sample information, that can be used by the computing module 540 to generate charts, graphs or other visual representations of the information outputted by the input device 550.

In one embodiment, the computing module 540 can execute on a computer to perform any of the estimation calculations and/or statistical or quality control analysis described herein. These statistical and/or estimation calculations can include any of the following: a determination of a reference gene cycle number; a determination of the number of two copy samples on the plate; a calculation of a measurement confidence; a calculation of a coefficient of variation between replicate samples or specimens taken from the same patient; a calculation of the standard deviation between replicate samples or specimens taken from the same patient; a calculation of a call confidence; a calculation of a reference gene slope; copy number estimates for each sample or specimen; a calculation of a delta cycle number for the plate; a calibration value; and any other calculations or determinations described herein. In some embodiments, the computing module 540 can store these calculations and determinations in the storage repository 530. In other embodiments, the computing module 540 can forward these calculations and determinations to a display module 560. These calculated and determined values can be included in a suite of quality control metrics. Thus, each value can be stored in an array, a database, a list or other data storage structure.

While in one embodiment the computing module 540 can be a single module, in other embodiments the computing module 540 can include one or more sub-modules, sub-routines or programs. In one embodiment, the computing module 540 can be a script executing on a computer. The script can, in some embodiments, execute within a master or parent program. For example, the computing module 540 can, in some embodiments, be a script executing within MATLAB. In this example, the computing module 540 can access a statistics library that includes one or more pre-defined programs or routines for carrying out the statistical analyses described herein.

The computing module 540, in some embodiments, can adjust any of the calculations or determinations using a calibrator or other adjustment value. Thus, in some embodiments a calibration or adjustment value can be added or subtracted from the values calculated and determined by the computing module to account for any of the following environmental concerns: variations resulting from the method used to obtain the specimen or sample; plate artifacts; artifacts present on other areas of the input device 550; temperature variations affecting the effectives of the assay; and any other environmental condition that may affect the integrity of data generated as a result of the assay. In some embodiments, a calculated standard deviation can be adjusted for the type of method used to obtain the specimen or sample. For example, if the sample is obtained by: acquiring a blood spot from a patient; swabbing the patient's mouth; obtaining umbilical cord blood; obtaining a chorionic villus sample culture; and obtaining amniotic fluid culture, the standard deviation may not have to be adjusted. On the other hand, if the sample is obtained from amniotic fluid or chorionic villus samples, a calculated standard deviation may, in some embodiments, have to be adjusted by 0.3. These adjustment values, in some embodiments, can be included in a configuration file stored in a storage repository 530 and used by the computing module 540 to determine whether a plate and/or a specimen passes a quality control check.

In one embodiment, the computing module 540, subsequent to carrying out one or more of the calculations and/or determinations described herein, can compare the resulting values to one or more reference values. These reference values, in some embodiments, can be threshold values or predetermined ranges. In one embodiment, these threshold values or predetermined ranges can stored in the storage repository 530. The values, in some embodiments, can be stored in any one of the following: a flat file; a database; a list; an array; a string including a concatenation of sub-string values; or any other data structure. In still other embodiments, the values can be stored in a temporary memory element until they are requested by the computing module 540.

In one particular example, a configuration file can include any of the following threshold values:

| Type of Threshold/Range/Adjustment | Value |
|---|---|
| Control Locus Threshold CT Value | 30 |
| Control Locus Slope Range | 0.15 to 0.55 |
| Zero Copy Number Call Range | −0.01 to 0.01 |
| One Copy Number Call Range | 0.6 to 1.4 |
| Two Copy Number Call Range | 1.6 to 2.4 |
| Three Copy Number Call Range | 2.435 |
| Two Copy Number Empirical Controls | 20 |
| Two Copy Number Standard Deviation Threshold | 0.1 |
| Sample CV Threshold | 0.15 |
| Measurement Confidence Threshold | 0.99 |
| Call Confidence Threshold | 0.9999 |
| Standard Deviation Adjustment for Bloodspot | 0 |
| Standard Deviation Adjustment for Mouth Swab | 0 |
| Standard Deviation Adjustment for Amniotic Fluid | 0.03 |
| Standard Deviation Adjustment for Amniotic Fluid Culture | 0 |
| Standard Deviation Adjustment for Chorionic Villus Sample | 0.03 |
| Standard Deviation Adjustment for Chorionic Villus Sample Culture | 0 |
| Standard Deviation Adjustment for Cord Blood | 0 |

In the above example, the threshold values, value ranges and adjustment values can be used to obtain one or more quality control metrics. These quality control metrics can be used to determine the statistical confidence in one or more estimated copy number values.

The computing module 540, in some embodiments, can apply quality control policies to one or more calculated or determined values to determine whether a plate should pass a predetermined quality control check and/or whether a specimen or sample should pass a predetermined quality control check. In some embodiments, the computing module 540 determines whether a plate and/or a specimen should pass a predetermined quality check by comparing the calculated and determined values to one or more predetermined thresholds and/or value ranges. While in some embodiments a quality control policy can include each of the threshold and value range requirements for a plate or a specimen, in other embodiments, each quality control policy can include a particular threshold or value range requirement. For example, a quality control policy can require that the coefficient of variation between four replicate specimens fall below a predetermined threshold value. This threshold value, in some embodiments, can be 0.15. In other embodiments, a quality control policy can require that a plate have: a number of two copy samples that falls above a predetermined value; a standard deviation between four replicate specimens that falls below a predetermined value; a mean call confidence value that is above or equal to a predetermined value; and that each control sample has a particular copy number call.

The storage repository 530, in some embodiments, can be any memory device, computing device or computer readable media. In one embodiment, the storage repository 530 can be any memory repository, computing device or computer readable media described herein. Communication between the storage repository 530 and any of the modules included in the analysis 510 system can occur over a network, communication bus or wire connection. In some embodiments, the storage repository 530 can read any information obtained, calculated or determined by the computing module 540 into memory. This data can be accessed by remote computing machines, computers within the analysis system 510, modules within the analysis system 510, or external media devices communicating with modules or computers within the analysis system 510.

In one embodiment, the computing module 540 can communicate with the storage repository 530 to access reference data, calibration data, report templates and other information. The computing module 540 can use the retrieved information to further carry out the methods and systems described herein and/or to generate display output that presents any of the information obtained, determined or calculated by the computing module 540. The computing module 540 can generate report content and in some embodiments, store that report content in the storage repository 530.

In some embodiments, an encoder executing within the analysis system 510 can encrypt, encode or compress received information prior to storing that information in the storage repository 530. In still other embodiments, cycle numbers and related information can be stored in a table, database, or list on the storage repository 530.

A display module 560 executing within the analysis system 510 can obtain report data or other output data from the storage repository 530 and/or the computing module 540. In one embodiment, the display module 560 can generate reports, user interfaces and other display templates to display the obtained report data and output data. Output data, in some embodiments, can include any information obtained from the input device 550, and any information calculated or determined by the computing module 540. The display module 560, in some embodiments, can include a browser, a form generator, or other program able to obtain and format data for display to a user.

In some embodiments, the display module 560 can interface with a display device 570 and/or another output device 555. The display module 560 can format received report and output data for display on the display device 570. In one embodiment, the display module 560 can format the output data and report data into a format that an output device 555 can use to generate an output signal.

The display device 570, in some embodiments, can be any display device. In other embodiments, the display device 570 can be any display device described herein. For example, the display device 570 can be a monitor, a hand-held computer, or any other machine or device having a display screen and able to render the display generated by the display module 560 and present the rendered image to a user. While FIG. 4 illustrates a display device 570 in communication with the analysis system 510, in some embodiments, the display device 570 can be included in the analysis system 510. Further embodiments include a display module 560 that includes the display device 570.

In some embodiments, the output device 555 can be used to output an audio, visual or other user-perceptible signal to a user. When the output device 555 receives data from the display module 560, in some embodiments, the output device 555 can sound an alarm or light one or more light emitting diodes or other lights to indicate whether the plate and/or the specimen passed each of the quality control metrics. For example, if an output value to indicate that the plate failed one of the quality control metrics, the output device 555 could illuminate an LED indicating the failure. In another embodiment, the output device 555 could output a digital message or sound an alarm when the plate fails one of the quality control metrics.

Figure 5A:
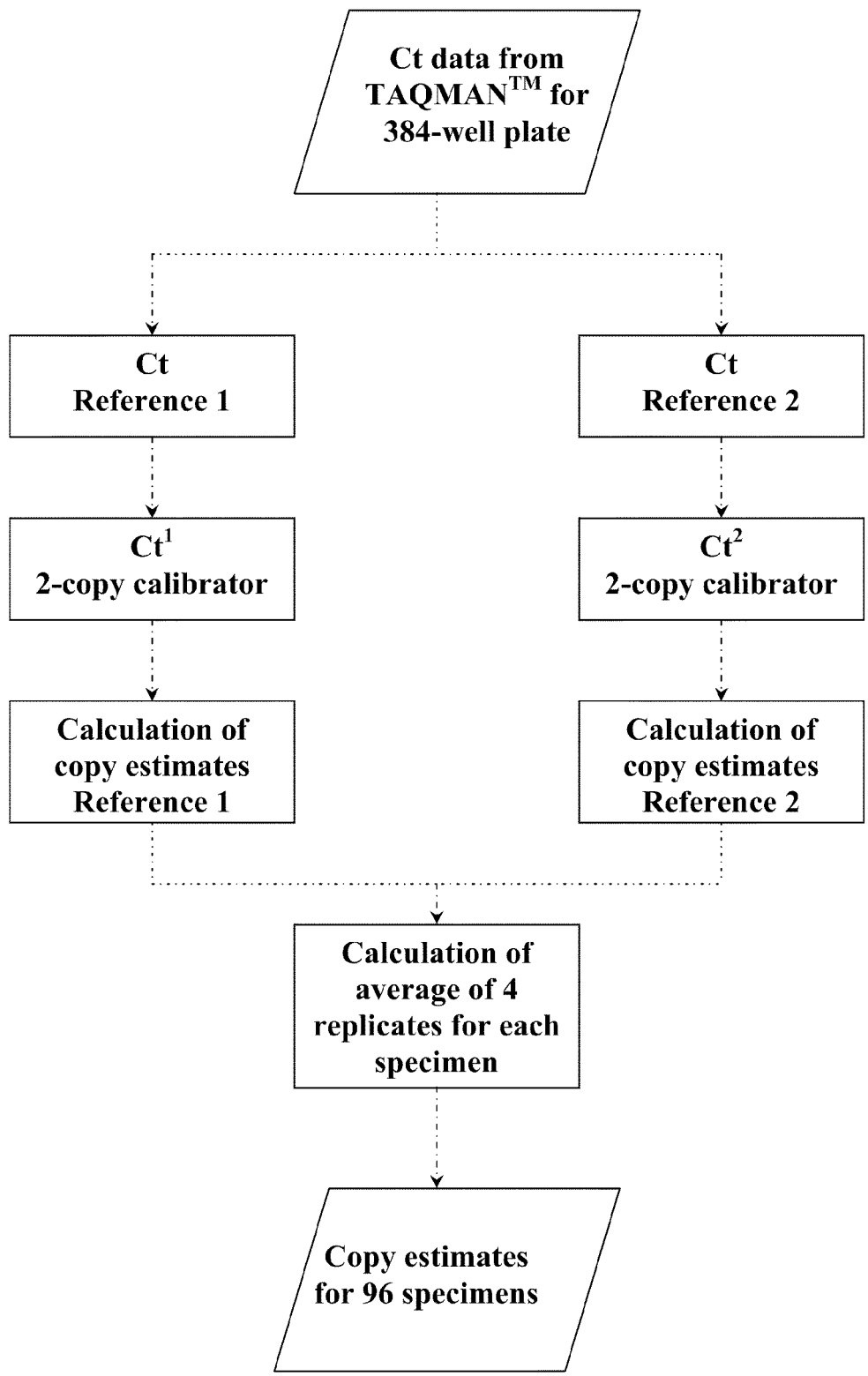
FIG. 5A is a flow diagram that illustrates an overview of certain embodiments of methods for obtaining copy number estimates for a set of specimens from Ct data from a TAQMAN™ real-time PCR experiment performed on replicates (4 replicates each for 96 specimens) on a 384-well plate
Figure 5B:
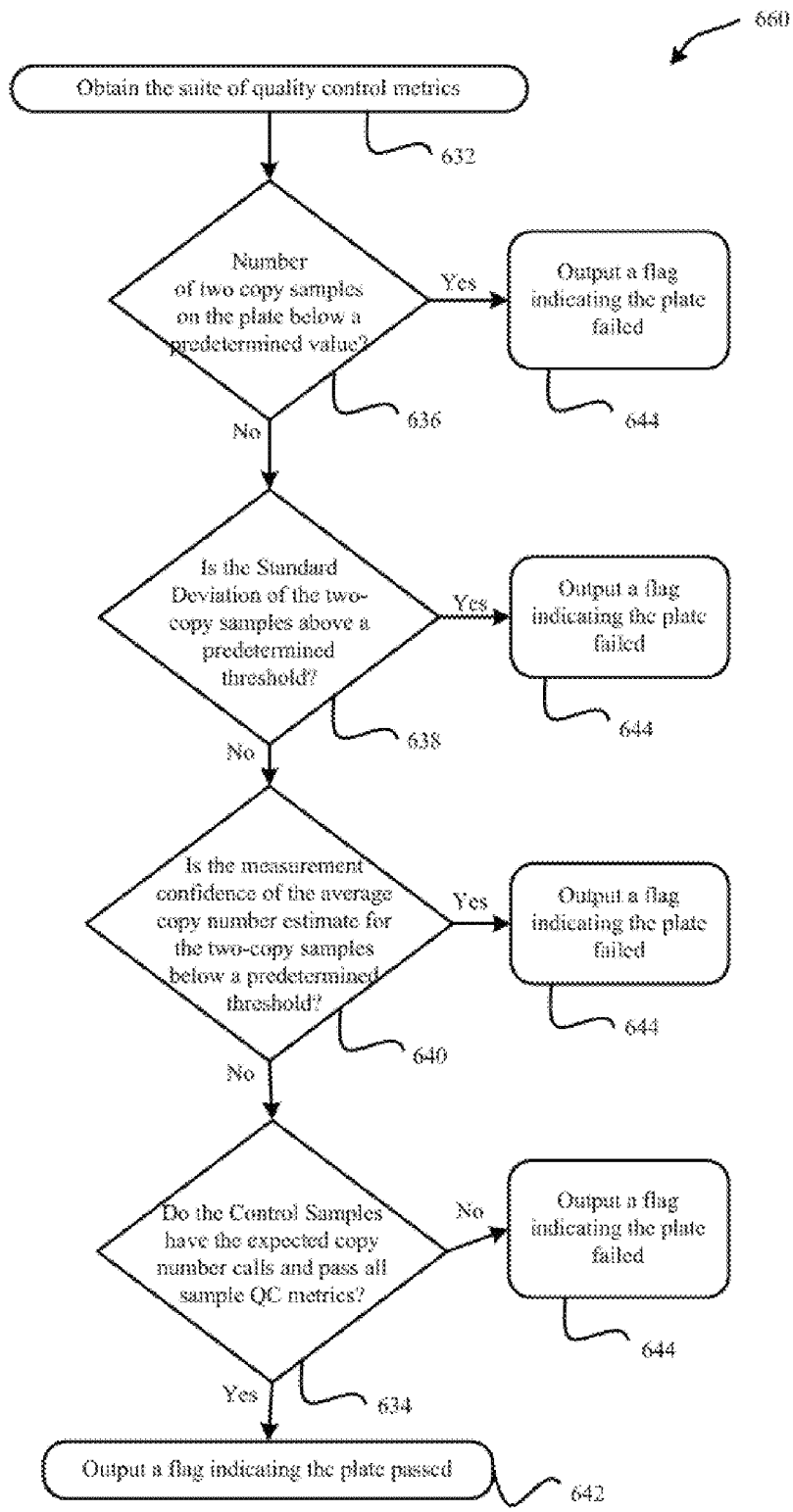
FIG. 5B is a flow diagram that illustrates an embodiment of a method for performing plate quality control.

Illustrated in FIG. 5B is one embodiment of a method 630 for applying plate quality control policies to one or more quality control metrics. In some embodiments, a computing module 540 or data analysis module (Not Shown) executing within the analysis system 510 obtains a suite of quality control metrics (Step 632) and determines whether the number of Z-copy samples (where Z is the number of copies of the reference locus, which in some embodiments is two) on the plate is below a predetermined threshold value (Step 636). If the number of Z-copy (e.g., two-copy) samples is below the threshold, then the computing module 540 or any other module outputs a flag indicating that the plate failed (Step 644). If the number of Z-copy samples does not fall below the predetermined threshold value, then the module determines whether the standard deviation for the Z-copy samples is above a predetermined threshold (Step 638). If the standard deviation is greater than the threshold, then the module outputs a flag indicating the plate failed (Step 644). If the standard deviation does not exceed the threshold, then the module determines whether the mean call for the Z-copy samples exceeds a predetermined threshold (Step 640). If the mean call exceeds a predetermined threshold, then the module outputs a flag indicating the plate failed (Step 644). If the mean call does not exceed the predetermined threshold, the module determines whether the control samples have the right copy number calls (Step 634). If the module determines that the control samples' copy number calls are below a predetermined threshold, then the module outputs a flag indicating the plate failed (Step 644). Otherwise, the module outputs a flag indicating the plate passed (Step 642).

Further referring to FIG. 5B, and in more detail, in one embodiment the method 630 can be carried out by the computing module 540. In other embodiments, the method 630 can be carried out by any combination of the following modules: the computing module 540 executing within the analysis system 510; a data analysis module (Not Shown) executing within the analysis system 510; or any other module executed by a processor within the analysis system 510.

FIG. 5B illustrates one embodiment of the process 630 where each step is consecutive such that each subsequent step requires the plate to pass the quality control test of the previous step. In other embodiments, each step can be independent such that execution of that step is not dependent on the determination that the plate passed the quality control test in the previous step. In still further embodiments, a group of steps within the method 630 can be dependent on each other, while a second group of steps can be wholly independent such that their execution is not dependent on the outcome of other steps included in the process.

In some embodiments, a module executing within the analysis system 510 retrieves the suite of quality control metrics (Step 632). The module, in some embodiments, can be the computing module 540. While in some embodiments, the module can calculate the quality control metrics; in other embodiments the module can obtain the quality control metrics from the storage repository 530. In some embodiments, the module can calculate a portion of the quality control metrics, and can obtain a portion of the quality control metrics from the storage repository 530.

Embodiments where a determination is made as to whether the plate passed a particular quality control test, can include outputting a flag or other indicator when the plate fails a particular quality control test (Step 644). In some embodiments, the flag can include a database entry, flag, signal, configuration setting or other variable indicating the test failed. This flag, in some embodiments, can be used by the computing module 540 to determine whether to continue testing the additional quality control metrics. In other embodiments, the computing module 540 can represent the flags in the report data content generated by the computing module 540. When the display module 560 generates an output display indicating whether the plate passed the quality control tests administered by the analysis system 510, the flags can be used to generate a user-perceptible display indicating whether the plate passed each administered test included in the associated policy.

A failed plate, in some embodiments, is a plate having quality control metrics that indicate poor quality copy number estimates. Thus, a failed plate can indicate that the calculated copy number estimates for the specimens on the plate are skewed and therefore the copy number estimates cannot be made.

The computing module 540, in some embodiments, can determine whether the number of samples on the plate that have two copies, is below a predetermined value (Step 636). In some embodiments, the computing module 540 can obtain a copy number estimate for each sample on the plate. Using this list, the module can determine how many samples have a copy number of two. If the number of samples having two copies falls below a predetermined threshold, then the plate is considered a failure (Step 644). In some embodiments, the determination made by the computing module 540 can be any determination described herein, that determines the number of two copy samples or specimens. In one embodiment, the predetermined threshold can be an empirically determined value, hard-coded into the system 510. In still other embodiments, the predetermined threshold can be a dynamically determined value based on historical data.

In one embodiment, the computing module 540 can obtain the standard deviation for the average of the two-copy samples. The standard deviation, in some embodiments, can be any standard deviation described herein. When the module determines that the standard deviation is above a predetermined threshold value (Step 638), the module 540 can fail the plate (Step 644).

In another embodiment, the computing module 540 can determine whether the measurement confidence for the average copy estimate for the two-copy samples is below a predetermined threshold value. When the measurement confidence is below a predetermined threshold value, the module 540 can fail the plate (Step 644).

In still another embodiment, the computing module 540 can determine whether the control samples or specimens have the right copy number calls (Step 634). This determination can be made using any of the calculations or determinations described herein. In one embodiment, determining whether the control samples have the right copy number calls can include determining whether the copy number calls falls below a predetermined threshold. When the call falls below the threshold, the module 540 can fail the plate (Step 644).

In some embodiments, the computing module 540 or another module can output a flag indicating that the plate passed each of the quality control tests (Step 642). Upon applying each of the quality control policies, and upon determining that the plate met each of the required standards, the module can output a flag, signal or other indicator indicating that the plate passed. While FIG. 5B illustrates a method 630 that outputs a plate pass flag, in some embodiments the method 630 may not include a step where the module outputs a plate pass flag.

Figure 5C:
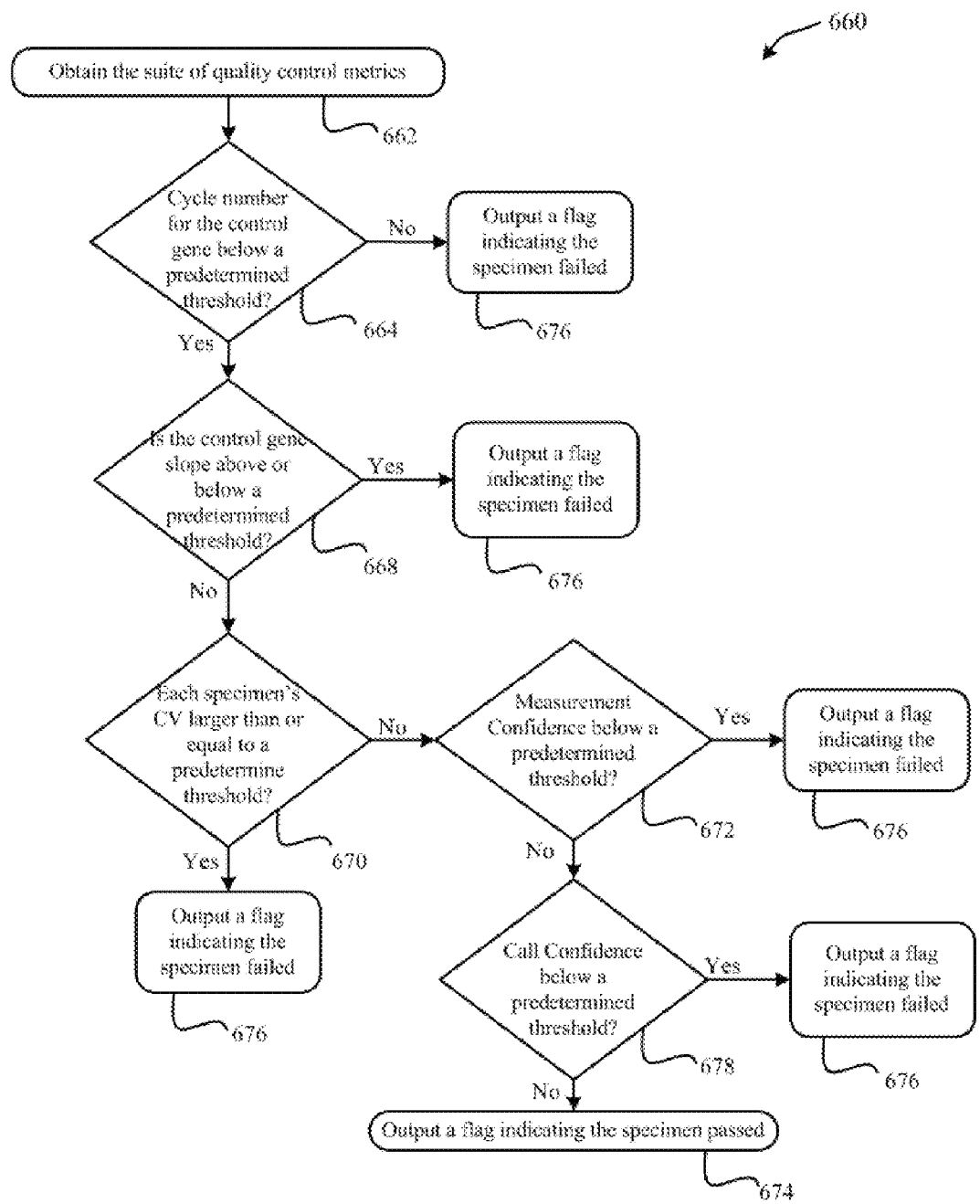
FIG. 5C is a flow diagram that illustrates an embodiment of a method for performing specimen quality control.

Illustrated in FIG. 5C is one embodiment of a method 660 for performing specimen quality control. In some embodiments, a computing module 540 can carry out any of the described steps. The module carrying out the method 660 is generally referred to as a module. In some embodiments, the module obtains a suite of quality control metrics (Step 662) and determines whether the cycle number for a reference gene or locus exceeds a predetermined threshold (Step 664). The module then determines whether the slope for the reference gene or locus is outside of a predetermined range (Step 668). A determination is then made as to whether the calculated coefficient of variation is larger than or equal to a predetermined threshold (Step 670). The module further determines whether a calculated measurement confidence falls below a predetermined threshold (Step 672) and whether a calculated call confidence falls below a predetermined threshold (Step 678). When the module determines that any of the above conditions is true for the specimen, the module can output a flag indicating the specimen failed (Step 676), otherwise the module outputs a flag indicating the specimen passed (Step 674).

Further referring to FIG. 5C, and in more detail, in one embodiment the method 660 can be carried out by the computing module 540. In other embodiments, the method 660 can be carried out by any combination of the following modules: the computing module 540 executing within the analysis system 510; a data analysis module (Not Shown) executing within the analysis system 510; or any other module executed by a processor within the analysis system 510.

FIG. 5C illustrates one embodiment of the process 660 where each step is consecutive such that each subsequent step requires the specimen to pass the quality control test of the previous step. In other embodiments, each step can be independent such that execution of that step is not dependent on the determination that the specimen passed the quality control test in the previous step. In still further embodiments, a group of steps within the method 660 can be dependent on each other, while a second group of steps can be wholly independent such that their execution is not dependent on the outcome of other steps included in the process.

In some embodiments, a module executing within the analysis system 510 retrieves the suite of quality control metrics (Step 662). The module, in some embodiments, can be the computing module 540. While in some embodiments, the module can calculated the quality control metrics; in other embodiments the module can obtain the quality control metrics from the storage repository 530. In some embodiments, the module can calculate a portion of the quality control metrics, and obtain a portion of the quality control metrics from the storage repository 530.

Embodiments where a determination is made as to whether the specimen passed a particular quality control test, can include outputting a flag or other indicator when the specimen fails a particular quality control test (Step 676). In some embodiments, the flag can include a database entry, flag, signal, configuration setting or other variable indicating the test failed. This flag, in some embodiments, can be used by the computing module 540 to determine whether to continue testing the additional quality control metrics. In other embodiments, the computing module 540 can represent the flags in the report data content generated by the computing module 540. When the display module 560 generates an output display indicating whether the specimen passed the quality control tests administered by the analysis system 510, the flags can be used to generate a user-perceptible display indicating whether the specimen passed each administered test.

A failed specimen, in some embodiments, is a specimen having quality control metrics that indicate a poor quality copy number estimate. Thus, a failed specimen can indicate that the calculated copy number estimate for that specimen is skewed and therefore a copy number call cannot be made for the specimen.

In one embodiment, the module can obtain the cycle number values for each reference gene or locus and determine whether the cycle number falls below a predetermined threshold (Step 664). The module, in some embodiments, can make this determination by applying a policy whereby the module determines whether the control locus cycle number is below a predetermined threshold, and/or within a predetermined range of cycle number values. When the control locus cycle number is below the threshold, the module can determine that the specimen failed (Step 676). In still other embodiments, the module can determine that the specimen failed upon determining that the cycle number value for a control locus exceeds a predetermined threshold ceiling value or when the cycle number value for a control locus falls below a predetermined threshold floor value.

In some embodiments, the module can determine whether a reference gene slope is within a predetermined range (Step 668). The reference gene slope can be any slope described herein. In some embodiments, a reference gene slope can be calculated and/or determined using any of the formulas or methods described herein. Upon calculating and/or obtaining the reference gene slope, the module can determine whether the slope falls below a predetermined threshold floor value or whether the slope exceeds a predetermined threshold ceiling value. When the reference gene slope falls outside of a predetermined range, the module can output a flag indicating the specimen failed (Step 676).

In one embodiment, the module determines whether the coefficient of variation for four replicate specimens of a target or control locus exceeds a predetermined value (Step 670). The coefficient of variation, in some embodiments, can be determined using the methods and formulas described herein. In some embodiments, when the module determines that the coefficient of variation is greater than and/or equal to a predetermined threshold value, the module can output a flag indicating the specimen failed (Step 676).

The module, in still another embodiment, can obtain the calculated measurement confidence and determine whether the calculated measurement confidence value is below a predetermined threshold (Step 672). The measurement confidence can be any measurement confidence value described herein, and can be calculated using any of the methods and formulas described herein. When, in some embodiments, the module determines the measurement confidence value falls below a predetermined threshold value, the module can output a flag indicating the specimen failed (Step 676).

In yet another embodiment, the module can obtain a calculated call confidence value to determine whether that value falls below a predetermined threshold (Step 678). In some embodiments, the call confidence value can be any call confidence value described herein, and can be calculated using any of the methods and formulas described herein. When, in some embodiments, the module determines the call confidence value falls below a predetermined threshold, the module can output a flag indicating the specimen failed (Step 676).

In some embodiments, the computing module 540 or another module can output a flag indicating that the specimen passed each of the quality control tests (Step 674). Upon applying each of the quality control policies, and upon determining that the specimen met each of the required standards, the module can output a flag, signal or other indicator indicating that the specimen passed. While FIG. 5C illustrates a method 660 that outputs a specimen pass flag, in some embodiments the method 660 may not include a step where the module outputs a specimen pass flag.

Displayed in FIGS. 7A-7B are screen shots illustrating a display of the quality control metrics and the outcome of the application of the plate and specimen control policies to the quality control metrics and other information obtained, determined or calculated by the computing module 540. In some embodiments, the displays illustrated in FIGS. 7A-7B can be displayed in a browser or application window. Other embodiments include a display rendered to fit on the screen of a portable computing device such as a smart phone, PDA or other hand-held device.

Figure 6A:
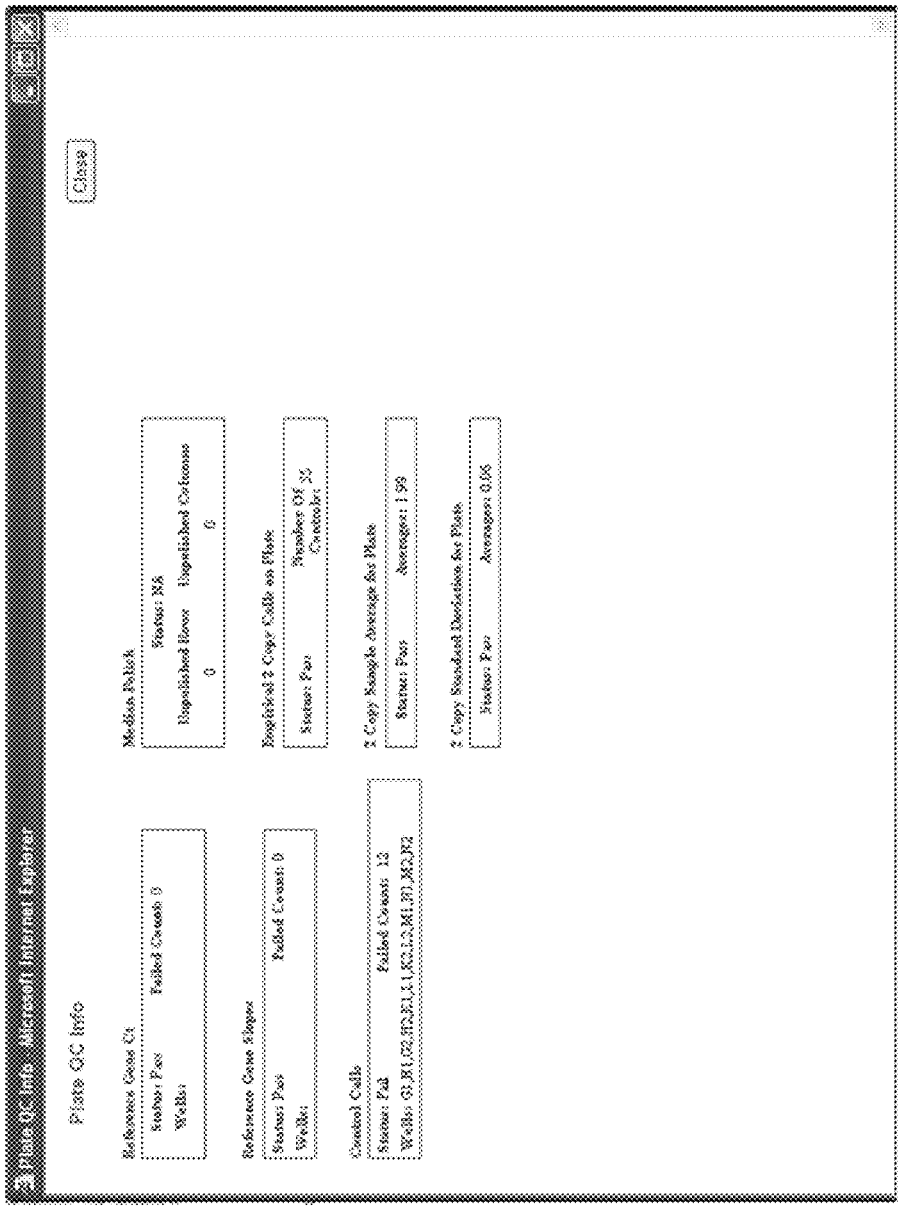

FIG. 6A illustrates a display screen that displays the quality control information reviewed to determine whether the plate passed the quality control test. In some embodiments, the following values can be displayed on the screen: the cycle number for the reference gene; whether the cycle number for the reference gene passed the above-described quality control test; the reference gene slope; whether the reference gene slope passed the above-described quality control test; the control samples and their status; the 2 copy sample averages for a plate; and the 2 copy standard deviation for a plate. In some embodiments, the display can be used to effectively inform a user of the outcome of the plate quality control tests.

FIG. 6B illustrates a display screen that displays the quality control information analyzed to determine whether a plate passed the quality control test. In some embodiments, the following values can be displayed on the screen: the copy number estimate; the call confidence level, whether the call confidence passed or failed; the measurement confidence level; whether the measurement confidence passed or failed; the sample coefficient of variation level and whether the coefficient of variation passed or failed. These values can be used by a user to determine whether the copy number estimates validly indicate that a target patient has or does not have a particular disease.

VI. Diagnostic Applications

In certain embodiments, methods disclosed herein are used in diagnostic applications.

In some embodiments, methods and/or systems of the invention are used to obtain a diagnosis with respect to status as a carrier of a disease, disorder, or condition. For example, individuals may be screened as carriers for genetic diseases. In some embodiments, normal individuals have two copies of a target locus. In some such embodiments, individuals having only one copy of a target locus are diagnosed as carriers.

In some embodiments, methods and/or systems of the invention are used in prenatal diagnostic applications. For example, a specimen containing prenatal nucleic acids (e.g., amniotic fluid, amniotic fluid/amniocyte cell cultures, chorioninc villus samples, chorionic villus cultures, maternal blood, etc.) may be assayed for copy number of a target locus. In some embodiments in which normal individuals have two copies of a target locus, a copy estimate of zero for a specimen may be used as an indication that the fetus has or is likely to develop a particular disease, disorder, or condition. Copy number estimation methods of the invention may be altered to account for possible heterogeneity in samples. For example, maternal blood may be expected to contain a mixture of fetal and maternal nucleic acids; thus the apparent copy number estimate of a target allele or target chromosome from maternal blood may be an intermediate between the copy number of the mother and that of the fetus.

In some embodiments, copy number estimates are obtained for individuals expecting to become parents, and, depending on the gene copy number estimate for the expecting parents, estimates are also obtained for their offspring (including unborn fetuses). For example, if copy number estimates indicate that one or more parents is/are a carrier for a genetic disease, depending on the dominant or recessive nature of the disease, a copy number estimate for the fetus is also obtained.

Diagnoses may be given with respect to a wide variety of aspects, of which carrier and disease status are but a few examples. As explained above, gene copy number estimates obtained by methods and systems of the invention may alternatively or additionally be useful for determining, e.g., altered risk of developing a disease or condition, likelihood of progressing to a particular disease or condition stage, amenability to particular therapeutics, susceptibility to infection, immune function, etc.

In certain embodiments, methods and systems of the invention are combined with other diagnostic methods and/or systems in order to obtain a diagnosis, or other methods may be used to confirm a diagnosis based on copy number estimates. For example, gene copy number estimates may be combined with one or more techniques such as sequencing (e.g., to determine mutations such as point mutations), karyotyping, and/or detection and/or quantitation of biological markers.

EXAMPLES

Example 1

TAQMAN™ Real-Time PCR to Determine a Patient's SMN1 Copy Number

In this example, a TAQMAN™ real-time PCR system is used to determine a patient's SMN1 copy number.

Experimental Design

Two primers that flank the SMN1 exon 7 locus are used for PCR amplification. A probe the recognizes an SMN1 sequence between the two primers is used to detect amplicon from exon 7 of SMN; the probe is labeled with an FAM fluorophore and contains a TAMRA quencher. This SMN1-specific FAM-TAMRA probe is released from the SMN1 probe during the extension portion of each round of PCR amplification by the exonuclease activity of the DNA polymerase. Liberation of the FAM fluorophore from the probe's TAMRA quencher allows lasers within the thermal cycle to excite the FAM fluorophore such that it emits light of a certain wavelength. The amount of light emitted is proportional to the amount of PCR product being generated.

Within this same reaction is a VIC-TAMRA probe and appropriate primers specific for a reference gene known to be always present in two copies per genome. The VIC fluorophore undergoes the same exonucleic release and laser excitation as does the FAM fluorophore, but its emission spectrum is distinguishable from that of FAM.

Software paired with the thermal cycling instrument can be used to make real-time plots of the accumulating FAM and VIC fluorescence data as a function of PCR cycle number. The number of cycles required to cross a fluorescence threshold is called the Ct (cycle threshold). In this example, the difference between the Ct for FAM (which corresponds to $Ct_T$ as described herein) and the Ct for VIC (which corresponds to $Ct_R$ as described herein) is $\Delta Ct$. $\Delta Ct$ should theoretically be approximately the same for all samples with two copies of SMN1. Because each cycle of PCR duplicates the template, DNA samples with one copy of SMN1 should have a $\Delta Ct$ that is one cycle greater (i.e., lags behind by one cycle) than samples with two copies of SMN1. Thus, it is possible to compare the ΔCt values of individual samples to the mean delta $\overline{\Delta Ct}$ of all samples on the plate to screen for carriers of one gene copy.

Controls

A No Template Control and four additional assay controls are used on each plate. Each control is represented twice on the plate. These controls may be obtained from verified cell lines and/or anonymized genomic specimens with known copy numbers of SMN1. Specifically, these controls have the following SMN1 genotypes: 0 copies of SMN1 (null), 1 copy of SMN1 (carrier), 2 copies of SMN1 (assumed 1+1 normal), 3 copies of SMN1 (assumed 2+1 normal).

The No Template Control/cocktail blank is 10 mM Tris pH 9.0 buffer, which is used to dilute patient samples.

Materials and Methods

Primers and Probes for Real-Time PCR for SMN1 and Reference Genes

Step 4: 60° C. for 1 min
Step 5: Go to Step 2, repeat 39 times
End

Example 2

Determining Copy Number of SMN1 Based on TAQMAN™ PCR Data

Ct values can be obtained from curves of signal versus time obtained, for example, from real-time PCR experiments performed according to Example 1. For each replicate on a plate, $Ct_R$ (cycle number for the reference locus) and $Ct_T$ (cycle number for the target locus; in this example, SMN1) are obtained as the cycle number required to reach the predetermined threshold fluorescence value, and ΔCt is computed according to Equation 1.

$$\Delta Ct = Ct_R - Ct_T \qquad \text{(Equation 1)}$$

| Oligo name | Sequence (5'→3') | Description |
|---|---|---|
| SMNFP | ATAGCTATTTTTTTTAATTCCTTTATTTTCC (SEQ ID NO. 1) | SMN1/2 forward primer for TaqMan amplicon |
| SMNRP | CTTACTCCTTAATTTAAGGAATGTGAGCA (SEQ ID NO. 2) | SMN1/2 reverse primer for TaqMan amplicon |
| SMN1DLprobe | FAM-AGGGTTTcAGACAAAATCAAAAAGAAGGAAG-TAMRA (SEQ ID NO. 3) | SMN1 specific TaqMan probe |
| SMN2Cprobe | PTO-AGGGTTTtAGACAAAATCAAAAAGAAG-GAAGG, -PO4, (SEQ ID NO. 4) | SMN2 specific competitive probe, (prevents binding of SMN1 probe to SMN2) |
| Smarcc1FP | AGGTACCACTGGAATTGGTTGAA (SEQ ID NO. 5) | SMARCC1 forward primer |
| Smarcc1RP | CATATATTAACCCTGTCCCTTAAAAGCA (SEQ ID NO. 6) | SMARCC1 reverse primer |
| Smarcc1DLProbe | VIC-, AGTACAAAGAAGCAGCACGAGCCTCTG, -TAMRA (SEQ ID NO. 7) | SMARCC1 specific probe |
| Supt5SFP | CACGTGAAGGTGATTGCTGG (SEQ ID NO. 8) | SUPT5 forward primer |
| Supt5RP | CGACCCTTCTATCCACCTACCTC (SEQ ID NO. 9) | SUPT5 reverse primer |
| Supt5DLProbe | VIC-, CGTTATCCTGTTCTCTGACCTCACCATG-TAMRA, (SEQ ID NO. 10) | SUPT5 specific probe |

Reagents for Real-Time PCR
100 μM stock PCR primer
100 μM stock FAM and VIC dual-labeled (DL) probes (ABI, stored at −20° C. away from light)
100 μM stock competitive probe
2× TaqMan Universal PCR Master Mix (e.g., ABI P/N 4364340)
0.2 μm filtered water
TAQMAN™ real-time pCR Conditions
Step 1: 50° C. for 2 min
Step 2: 95° C. for 10 min
Step 3: 95° C. for 15 sec Table 3 shows exemplary calculations for ΔCt for a number of replicates on the same plate. Typically, many more replicates will be used in each plate than shown in Table 3.

TABLE 3 exemplary Ct calculations for replicates on plate.

| Well | ≈$Ct_r$ | ≈$Ct_t$ | ≈ΔCt |
|---|---|---|---|
| 1 | 24.1 | 24.2 | −0.1 |
| 2 | 23.8 | 23.7 | 0.1 |

TABLE 3-continued exemplary Ct calculations for replicates on plate.

| Well | ≈$Ct_r$ | ≈$Ct_t$ | ≈ΔCt |
|---|---|---|---|
| 3 | 24.5 | 24.6 | −0.1 |
| 4 | 23.7 | 23.9 | −0.2 |
| 5 | 23.8 | 24.3 | −0.5 |
| 6 | 24.0 | 24.2 | −0.2 |
| 7 | 24.4 | 24.3 | 0.1 |
| 8 | 24.1 | 25.2 | −1.1 |
| 9 | 23.9 | 23.8 | 0.1 |
| 10 | 24.2 | 24.4 | −0.2 |

The calibrator value $\overline{\Delta Ct}$ is then calculated according to Equation 4 as the 80% trimmed mean of the ΔCt values. For the ΔCt values in Table 3, $\overline{\Delta Ct}$ would be the average ΔCt values for wells having the middle 20% of values (e.g., −0.1 and −0.2), in other words, $\overline{\Delta Ct}$ for the plate would be approximately −0.15.

Copy number is then estimated for each well according to linear scale:

$$\text{(Linear scale) } T_{Ci} = Z \cdot 2^{(\Delta Ct - \overline{\Delta Ct})}$$

For example, for well 1, copy number of SMN1 ($T_C$) would be estimated as $$T_C \cong 2 \cdot 2^{(-0.1 - (-0.15))} \cong 2 \cdot 2^{(0.05)} \cong 2 \cdot 1.035 \cong 2.07$$

For well 8, copy number of SMN1 ($T_C$) would be estimated as $$T_C \cong 2 \cdot 2^{(-1.1 - (-0.15))} \cong 2 \cdot 2^{(-0.95)} \cong 2 \cdot 0.518 \cong 1.04$$

Example 3

Assessing Quality of Copy Number Estimates for SMN1 Gene

In this Example, quality of copy number estimates for the SMN1 gene is assessed using an algorithm and quality control metrics.

An overview of algorithm calculations described in this example is shown in FIG. 5A. As depicted in FIG. 5A, Ct data from a TAQMAN™ experiment on a one or more 384-well plates containing 4 replicates each of 96 specimens can be used to obtain copy estimates for 96 specimens. An estimation of the gene copy number for each sample is performed. The algorithm calculates the ΔCt values (Ct differences between SMN1 and the reference gene probes) for all wells on a plate. Copy number estimates are subsequently derived based on the exponential model of the PCR amplification that depends on the reference gene calibrators. The calibrators are the average Ct differences between SMN1 and the reference genes for samples with two SMN1 copies and are calculated as the 80% trimmed averages of the plate ΔCt values. In the final step of the calculations, the copy number estimate for each sample is calculated as the average over the four reactions.

FIG. 5B depicts an overview of the plate quality controls employed to assess quality of copy number estimates. Overall quality of the plate is assessed in two ways. First, copy number values for the control samples are checked against their known values. The plate is failed if the data quality of the control samples or the calculated copy numbers do not match the known values. Second, the plate is failed if the number of two gene copy samples is less than a validated threshold, or the standard deviation of the two gene copy samples is above a validated threshold, or if the measurement confidence for the average copy number estimate of the two-copy samples is below a validated threshold.

FIG. 5C depicts an overview of specimen quality controls (QC) employed to assess quality of copy number estimates. Five QC metrics are derived for each specimen. The first three metrics assess the quality of the data being analyzed. The reference gene Ct values, reference gene amplification curve slopes, and the coefficient of variation (CV) of calls derived from the replicate reactions are evaluated against validated thresholds. The sample is failed if the results of any one of these are outside of the valid thresholds. Confidence of each sample result is measured by two statistical metrics, call confidence and measurement confidence. These metrics provide confidence in the resultant copy number estimates based on inter- and intra-sample variability on the plate.

Description of an SMN1 test data analysis module, as well as a detailed documentation of calculation of call estimates in the module, is provided below.

I. SMN1 Test Data Analysis Module
Summary of Content
  A. Data analysis quality control metrics
    1. Plate quality control
    2. Sample quality control
  B. Data analysis algorithm
    1. Error handling
    2. Data input
    3. Sample name processing
    4. Slope calculation
    5. Slope QC and Ct QC
    6. Calculation of delta Ct, averaging of the well replicates and median polish
    7. Measurement confidence
    8. Sample coefficient of variation
    9. Two-copy number average and standard deviation
    10. Sample type adjustments
    11. Call confidence
    12. QC testing of controls
    13. Module output
  C. Data analysis module output format
    1. Plate QC
    2. Sample QC
  D. Recommendations for Operations QC
  E. Data analysis module output format
  F. Data analysis executable file
    1. Run time requirements
    2. Command line format
    3. Input
    4. Output
  G. Configuration file
  H. Calculation of the copy number limits
  I. Matlab compilation requirement
  A. Data Analysis Quality Control Metrics
    1. Plate Quality Control
  Plate quality control ensures that control samples perform as specified and verifies that the information needed for the data analysis module is present on the plate.
  Control Samples QC:
    a. Reference gene Ct check: Plate QC verifies the reference gene Ct in each reaction for the control samples is less than the specified threshold (30 in the configuration file). If a control sample well has the reference gene Ct above or equal to the threshold, a plate alert is generated with a list of failed control sample wells. Blank controls are excluded.
    b. Reference gene slope check: Plate QC verifies the reference gene fluorescence curve slopes of the control samples are within the specified limits for each of the four reactions ([0.15, 0.55) in the configuration file). If a control sample well has the reference gene slope outside the specified limits, a plate alert is generated with a list of failed control sample wells. Blank controls are excluded.

c. Control sample call check: Plate QC verifies the copy number estimates for the control samples pass the measurement confidence test for the correct copy number value (99.99% confidence), the call confidence test (99.99% confidence) and the sample CV test (0.15). If any of the control samples do not pass the measurement confidence test, a plate alert is generated with a list of the wells for the failed control samples. Blank controls are excluded.

Plate-wide QC checks that are used before the statistical methodology is applied:

d. The number of the two-copy samples: Plate QC confirms that the number of two-copy samples that passed the reference gene Ct, reference gene Slope, measurement confidence, call confidence and sample CV tests (good quality samples) is adequate for the statistical analysis (20 samples). The number of two-copy samples is exported by the data analysis module. If the number of two-copy samples is less than the threshold, a plate alert is generated.

e. The average of the two-copy samples: Plate QC verifies that the average of the good quality two-copy samples passes the measurement confidence test. If it does not, a plate alert; is generated. The average is exported by the data analysis module.

f. The standard deviation of the two-copy samples: Plate QC checks if the standard deviation of the good quality two-copy samples is less than a specified threshold (0.1). If It is larger than or equal to the threshold, a plate alert is generated. The standard deviation is exported by the data analysis module.

2. Sample Quality Control

The following QC checks are performed for each sample on the plate including the control samples.

a. Reference gene Ct check: Sample QC verifies the reference gene Ct for each of the four wells is less than the specified threshold (30). If a sample well has the reference gene Ct above or equal to the threshold, a sample alert is generated with a list of failed wells.

b. Reference gene slope check: Sample QC verifies the reference gene fluorescence curve slopes are within the specified limits ([0.15, 0.55]) for each of the four wells. If a sample well has the reference gene slope outside the specified limits, a sample alert is generated with a list of failed wells.

c. Sample CV check: Sample QC calculates the sample CV between the four replicate measurements of copy number estimates. If the sample CV is larger than or equal to the specified threshold (0.15), a sample alert is generated.

d. Measurement confidence: Sample QC calculates a measurement confidence estimate. Measurement confidence is the statistical confidence level for the sample copy number estimate being within the copy number limits. If the confidence is lower than the specified threshold (99%), a sample alert is generated.

e. Call confidence: Sample QC calculates a call confidence. Call confidence is the statistical confidence level for the sample to have the number of the SMN1 gene copies reported in the output. If the call confidence is lower—than the specified threshold (99.99%), a sample alert is generated.

B. Data Analysis Algorithm

This description of the data analysis workflow follows the steps of the algorithm implemented in the SMA data analysis module. There are three basic parts in the algorithm, processing of the raw data, statistical analysis, and QC analysis.

1. Error Handling

The data analysis module exports error messages in the log file. The name of the log file follows the following nomenclature; it begins with the "SMADALog" prefix and continues with the Ct data file name. If the Ct data file name is not specified in the algorithm arguments, the module creates the log file, "SMADALog_Default.txt." The log file is empty if the module has successfully processed the data. If the algorithm encounters an error or an unexpected intermediate result, it stops the calculations and writes an error message in the log file.

2. Data Input

The SMA data analysis module requires two input data files, Ct data from TaqMan and clipped data from TaqMan. The files should be in the standard ABI format. The module begins data input with the Ct data file. It searches for a line beginning with the "Well" keyword, and inputs 384 lines after the "Well" line. These are the FAM Ct measurements. After it processes FAM, it searches for the "Well" keyword again and imports another 384 text lines after the keyword. These are the VIC Ct measurements. Lines in the Ct data file are parsed for the three variables; sample name, reporter, and Ct. All non-numerical Cts are converted to 40.

The clipped data file is read as a tab delimited file. The module read the block AS3 . . . CF770. This block contains delta fluorescence measurements for two channels in 384 wells for 40 cycles. The cells in the block must contain numeric values.

If the module can not open any of the two data files, it generates an error message and stops data processing. No wells can be omitted before the algorithm processing.

3. Sample Name Processing

Upon reading sample names from the Ct data file, the algorithm parses the names for the sample ID, the sample type and the well location. The algorithm breaks up the sample name by the vertical bar "l". The string before the first vertical bar is assigned as the sample ID, the string between the first and the second vertical bar is assigned as the sample type, and the string after the second vertical bar is discarded. Empty wells should have empty sample names, " " in the Ct data file. The sample type identifiers should follow the sample type convention: BLDPER, BLOODSPOT, MOUTHWASH, AMNIO, CULTAFCEL, CVS, CVSCULT, CORDBLOOD. Empty sample types are assumed to be SURER. Unrecognizable sample types are assumed to be BLDPER but are not included.

4. Slope Calculation

Slope calculation for the VIC channel is performed based on the three cycle measurements closest to the Ct measurement reported in the Ct data file. The equation for the calculation is as follows:

$$S = \frac{Y_3 - Y_1}{2}$$

Where Y1, Y2, Y3 are the three (log-transformed, background normalized) delta fluorescence measurements.

5. Slope QC and Ct QC

The algorithm checks the slope and the Ct measurements for the reference gene channel (VIC). The module generates test results for each sample including the control samples if the slope or the Ct value do not pass the QC metrics. For sample that failed this QC test, the algorithm records the wells where the QC metrics failed.

6. Calculation of Delta Ct, Averaging of the Well Replicates and Median Polish The algorithm calculates delta Cts by subtracting the FAM Ct value from the VIC Ct value, For each of the control amplicons the algorithm calculates the trimmed mean delta Ct between the VIC and the FAM channels of the specimen samples (control and empty wells are excluded in this calculation) where 80% of the observations in the tails of the empirical distribution are trimmed or removed from the calculation. Based on the trimmed means the algorithm derives copy number estimates on the log and the linear scale according to Equation 5 (linear scale) and Equation 6 (log scale).

Linear scale $T_C i = 2 \cdot 2^{(\Delta Ct - \Delta \overline{C}t)}$ (Log scale) $T_{Ci} = 2 + \Delta Ct - \Delta \overline{C}t$ If the plate is full, the algorithm performs median polish on the log scale copy number estimates. Upon completion, the module checks if any of the rows or columns has been adjusted for more than 0.2 units. The adjustments for these rows and columns are reverted if their replicate row or column also fails the median polish cut-off. Columns 1 and 2 are always excluded from polishing. The row and column numbers are reported in the Plate QC output.

Copy number estimates on the linear scale are regenerated after median polish to include the adjustments.

The copy number estimates for the four wells for each sample are averaged at this point. Copy number calls are calculated by rounding off the average copy number estimates with two exemptions. Copy number call for the BLANK controls is defaulted to "—". The copy number calls are limited at three; calls larger than three are substituted with three copies. The mean and the standard deviation for each sample on the plate are stored on the log and the linear scales.

7. Measurement Confidence

The assumption of normality of the sample average across the four replicate wells is made for this calculation. The measurement confidence is determined as the largest normal confidence interval around the copy number estimate (averaged across the four wells) that would fit within the copy number limits for a particular sample. In other words, measurement confidence looks at variability and the mean between the four replicate measurements for each specimen or control. It is a measure of intra-sample variability. The parameters for the normal distribution are as follows: the mean is the average copy number estimate across the four wells on the linear scale. The standard deviation is the standard error of the mean. The limits are the copy number limits specified in the configuration file. The Sample QC procedure checks if the measurement confidence is high enough for a sample to be of the good quality. If the measurement confidence is lower than the cut-off, the measurement confidence QC metric for this sample is failed.

The measurement confidence and the status of the measurement confidence QC test are exported into the output file.

8. Sample Coefficient of Variation

Sample CV is calculated on the linear scale and is the ratio of the sample standard deviation and the sample mean between the four replicates. Sample CV for zero copy samples are calculated differently due to the potential division by zero. Sample CV for a zero copy number sample is calculated as the ratio of the standard deviation and the mean plus one. The sample QC procedure checks if the sample CV is lower than the threshold specified in the configuration file. If the CV is larger than or equal to, the sample CV QC metric is failed for this sample.

The sample CV and the status of the sample CV QC test are exported into the output file.

9. Two-Copy Number Average and Standard Deviation

For the derivation of the call confidence values, the algorithm calculates the background variability. The background variability is the variance of the call estimates for two-copy samples. In certain embodiments, there is a certain number of two-copy samples that is required by the algorithm and this number is specified in the configuration file. For the estimation of the standard deviation and the mean, the module pools only good quality samples, i.e., satisfy the following requirements:

(a) passed the VIC Ct, VIC Slope, Measurement confidence, and sample CV QC tests
(b) not a control
(c) estimated to have two copies of the SMN1 gene
(d) BLDPER sample type If the number of such samples is below the threshold, requirement (d) is removed and all sample types are pooled together. The number of the good quality two-copy samples is reported in the output file along with their average and the standard deviation.

A metric similar to measurement confidence it derived for the average of these samples based on the standard error of the mean. If confidence around the two-copy samples' average is below the threshold set in the configuration file, Plate QC fails the two-copy average test.

10. Sample Type Adjustments

The two-copy samples standard deviation is the standard deviation used in the West to derive the call confidence values. Since different sample types may potentially display different variability in the test, standard deviation adjustments can be specified in the configuration file. Each sample type can have an adjustment. The adjustment is added to the estimated two-copy sample standard deviation in order to calculate the sample type specific standard deviation. If requirement (d) is removed in step 9, the adjustments are not performed. Currently, only the AMMO and CVS standard deviations are adjusted by 0.03 units.

11. Call Confidence

Call confidence is calculated from t-test p-values. The algorithm makes the following assumptions, call estimates are normally distributed and have equal variances across the copy numbers. A critical number (20) of two-copy samples excluding the controls is needed before this calculation can be performed. For each sample, the algorithm determines t-test p-values for the sample's being from the adjacent copy number distributions, e.g., for a sample with two-copy numbers, it calculates the p-value for the copy number estimate to come from the one copy number distribution or the three copy number distribution. The two t-test p-values are summed and the confidence is calculated by subtracting the sum of the two p-values or the single p-value in the case of zero or three copy numbers from 1—a large p-value corresponds to low confidence.

The copy number t-distribution means are determined by averaging all of the copy number estimates for that particular number of gene copies. If there are not any estimates for a particular gene copy number, the means are assumed to be −2, 1, 2, and 2.585. The copy number t-distribution standard deviations are the sample type adjusted-standard deviations and they vary for different sample types.

When call confidence is calculated for each sample, call confidence QC test is performed. If the call confidence is less than the threshold specified in the configuration file, the call confidence test fails for that sample. The call confidence test status and the call confidence value are exported into the output file.

12. QC Testing of Controls

Blank controls are excluded from this part of the QC process. Every control sample is checked for the quality of the reference gene (VIC channel) Ct, reference gene Slope, measurement confidence, call confidence, and sample CV. If any of these sample QC metrics failed, a plate alert is generated with a list of failed wells and the failed metrics. The control sample copy number estimates are also checked for their correspondence with the expected copy number values. The module finds the controls by well location based on the final SMN1 plate layout.

13. Module Output

The data analysis module begins the output with the plate. QC metrics and continues with the sample QC metrics and data analysis results. Samples are exported by columns so that the control samples are written first in the file. Information about empty wells is not exported into the output file.

C. Recommendations for Operations QC

Failures of certain QC metrics may indicate suboptimal performance of the instruments, automation scripts, or the assay reagents. Below is a list of failures that may require immediate attention of the Operations QC group.

1. Standard deviation of the 2 copy samples exceeding the threshold in Plate QC. Sporadic failure of this Plate QC metric may indicate a problem with the assay reagents or reagent dispensing. Consistent failure of this Plate QC metric should trigger reagent and instrumentation performance quality reassessment. Failure may also indicate a problem with the DNA extraction.

2. Percentage of non-called (repeated) samples. A spike increase above 25% in the repeat sample rate on a plate may indicate suboptimal performance of the reagents or a problem with liquid dispensing/mixing. A consisted repeat rate above 20% for a plate batch is important and may require immediate attention of Operations QC. It may indicate poor reagent quality or a problem with the instrumentation hardware or software.

3. Failure of controls. Consistent failure of more than two control samples in a plate batch is critical and requires immediate attention of Operations QC. It may likely indicate failure of the control samples, if the overall plate repeat rate is below 10%.

4. Location failure. Consistent failure of samples at a particular location on the plate requires immediate attention of Operations QC. It likely indicates suboptimal performance of the instrumentation hardware at that location.

D. Data Analysis Module Output Format

The SMA Data Analysis output is in XML format. It consists of two parts, Plate QC and Sample QC. The XML file begins with a standard formatting line:

<?xml version="1.0" encoding="UTF-8" ?>

Followed by the global SmaResults structure with the plate, run numbers and the module version:

<SmaResults plateNumber="32008" runNumber="123456" moduleVersion="0.2"> </SmaResults>

Plate QC structure is contained in:
<PlateQc> </PlateQc>

Sample QC structure is contained in:
<SampleQc> </SampleQc>

1. Plate QC (a) <VicCt> object displays the status of the reference CT measurement test for the control samples, additionally if the test fails it lists the failed wells.

(b) <VicSlopes> object displays the status of the reference Slope measurement for the control samples, if the test fails it lists the failed wells.

(c) <ControlCalls> object displays the status of the controls. If any of the control calls do not match the designated number of gene copies and does not pass all of the sample OC metrics, the wells for the failed controls are shown inside the structure.

(d) <MedianPolish> object displays the status of the Median Polish procedure. Non-polished rows and columns, if any, are displayed inside the structure.

(e) <EmpiricalNegative> object displays the number of the two-copy samples on the RJ plate. If the number is below the threshold, the test fails.

(f) <NegativeAverage> object displays the mean call for the two-copy samples. The test fails if the mean with its confidence interval is outside of the acceptable limits (g) <NegativeStdiv> object displays the standard deviation of the two-copy samples. The test fails if the standard deviation is above the threshold.

2. Sample QC a. <Samples> object lists all the control and test samples on the plate.

b. <Sample> object contains individual samples and displays the following information:
  i. Sample ID|sample type in sampleID
  ii. Sample type (Control, Specimen) in type
  iii. Copy number value in copyEstimate
  iv. Sample copy number call in call. Blank controls have their copy number calls defaulted to "—".
  v. Status of the call confidence test (Pass or Fail) in callConfidenceCriterion
  vi. Measurement confidence in measurementConfidence
  vii. Status of the sample CV test (Pass or Fail) in sampleCvCriterion
  viii. Sample CV in sampleCv
  ix. VIC CT test status for this sample with a list of failed wells in VicCt
  x. VIC Slope test status for this sample with a list of failed wells in VicSlopes
  xi. Sample FAM DeltaRn data on the log 10 scale for the four wells in FAM: Well position in well and Log 10 DeltaRn numbers in cycle 1 through cycle 40
  xii. Sample VIC DeltaRn data on the log 10 scale for the four wells in VIC: Well position in well and Log 10 DeltaRn numbers in cycle 1 through cycle 40

E. Data Analysis Executable File (SMADataAnalysis.exe)

SMADataAnalysis.exe is a Matlab (Mathworks, Inc) script compiled in the Win32 environment. SMADataAnalysis performs data normalization, call assignment, and calculates call confidence for SMN1 TaqMan data.

1. Run Time Components a. Matlab run time libraries. MCRInstaller.exe is needed to run the script on a Windows workstation. The version of the MCRInstaller.exe file should match the version of Matlab used to compile the script.

b. SMADataAnalysis.ctf. The file contains a set of Matlab functions used while the script runs. This file needs to reside in the SMADataAnalysis.exe folder. Upon the first execution of the script will unpack the ctf file into the SMADataAnalysis_mcr subfolder. Once the subfolder is created.

c. SMADataAnalysis.cfg. The file is a configuration file. It is in a plain text format and contains various adjustable thresholds for the QC metrics.

2. Command Line Format

SMADataAnalysis [CT Data File] [Clipped Data File] [Output File] (Plate #1 [Run #]
 a. CT Data File is an ABI CT data output file in the standard text format.
 b. Clipped Data File is the corresponding ABI clipped data file with the Rn and
DeltaRn measurements in the standard text format.
 c. Output File is the output file name.
 d. Plate # is the plate number.
 e. Run # is the run number.
3. Input
 a. CT data file
 b. Clipped data file
 c. Output file name
 d. Plate number
 e. Run number
 f. Configuration parameters from the configuration file
4. Output SMADataAnalysis.exe writes output into two files:
 a. The output file specified in the command line (see the format description in the SMA Data Analysis Output file format.doc)
 b. The log file, "SMADALog_[CT Data File]". The log file registers abnormal intermediate results during the calculations and general code execution errors. On a successful execution the log file should be empty.

F. Configuration File

The configuration file, SMADataAnalysis.cfg is a text file where the QC metric thresholds and other parameters are specified. The file should have, the following lines:
 VIC Channel Ct Threshold: 30
 VIC Channel Slope Range: [0.15 0.55]
 Zero Copy Number Call Limits: [−0.01 0.01]
 One Copy Number Call Limits: [0.6 1.4]
 Two-copy Number Call Limits: [1.6 2.4]
 Three Copy Number Call Limits: [2.43 5]
 Minimal Number of Two-copy Number Empirical Controls: 20
 Two-copy Number Standard Deviation Threshold: 0.1
 Sample CV Threshold: 0.15
 Measurement Confidence Threshold: 0.99
 Call Confidence Threshold: 0.9999
 Standard Deviation Adjustment for BLOODSPOT: 0
 Standard Deviation Adjustment for MOUTHWASH: 0
 Standard Deviation Adjustment for AMMO: 0.03
 Standard Deviation Adjustment for CULTAFCEL: 0
 Standard Deviation Adjustment for CVS: 0.03
 Standard Deviation Adjustment for CVSCULT: 0
 Standard Deviation Adjustment for CORDBLOOD: 0

VIC Ct 30 is the current Ct threshold for the reference gene channel.

The range in the brackets for the VIC Channel Slope Range is the allowed variation range for the reference gene slope on the log 10 scale.

Copy number call limits are shown in the brackets for the different copy number estimates.

As shown above, configuration parameters also include the minimal number of the two-copy samples used for the estimation of the variance in the call confidence calculation, the maximal allowed standard deviation for the two-copy samples, the maximal allowed sample CV, allowed confidence levels, and variability adjustments for different sample types.

G. Calculation of Copy Number Limits

Recalculation of the copy number limits is not recommended but may be performed for new reagent lots, new instruments or other changes in the experimental conditions. In some embodiments, 30+ individual reaction call estimates for one biological specimen for each of the four copy numbers: 0, 1 2, and 3 are obtained.

The procedure for calculation of the copy number limits is as follows:

1. The call estimate measurements for individual reactions are transformed to fit a standard beta distribution:

0 copy call estimates between 0 and 0.5 are multiplied by 2. The measurements outside of the [0, 0.5] interval are discarded.

1 copy call estimates between 0.5 and 1.5 are reduced by 0.5. The measurements outside of the [0.5, 1.5] interval are discarded.

2 copy call estimates between 1.5 and 2.5 are reduced by 1.5. The measurements outside of the [1.5, 2.5] interval are discarded.

3 copy call estimates between 2.4 and 3.4 are reduced by 2.4. The measurements outside of the [2.4, 3.4] interval are discarded.

2. Mean and the variance are calculated for each of the transformed copy number data sets.

3. Separate beta distributions are fit to the copy number transformed data by estimation of alpha and beta $$\alpha = \mu \left[ \frac{\mu(1-\mu)}{\sigma^2} - 1 \right];$$

$$\beta = (1-\mu) \left[ \frac{\mu(1-\mu)}{\sigma^2} - 1 \right]$$

The beta distribution family was chosen for this procedure because of its asymmetry and bounded support.

4. Distributional limits are obtained by calculating the 0.00005 and 0.99995 percentiles for the four distributions and reverse-transforming the percentiles into the original scale. For example, 1.5 is added to the 0.00005 and 0.99995 percentiles for the 2 copy number distribution.

5. Distributional limits are checked against the limit boundaries:
 0 copy
  The upper limit within [0.01, 0.1]
  The lower limit is set as the negative upper limit.
 1 copy
  The upper limit within [1.4, 1.45]
  The lower limit within [0.5, 0.6]
 2 copy
  The upper limit within [2.35, 2.4]
  The lower limit within [1.6, 1.65]
 3 copy
  The lower limit within [2.4, 2.5]
  The upper limit is set at 5.

The limit boundaries are set up to insure that the proper call estimate ranges are captured by the limits and there is a sufficiently wide indeterminate range between consecutive copy number regions. The placement of the boundaries is based on the variability of the call estimates for confirmed samples in the test development and the VeVa.

I. Matlab Compilation Requirements

The module is successfully compiled in Matlab v. R2007a. The module compilation requires Matlab, Statistical Toolbox, Matlab Compiler. Below is the list of Matlab files with the module source code:

1. SMADataAnalysis.m—the main script that is called from the command line.
2. SMAAnalysisModule.m—the main calculation script. It is called from SMADataAnalysis.m
3. medianpolish.m—the median polish function.
4. alignReplicates.m—the replicates processing function.
5. ReadConfig.m—the function for reading parameter values from the configuration file.

II. Detailed Documentation of the Calculation of Call Estimates in the SMA Data Analysis Module Delta Cts are calculated for each well (i,j) on the plate according to equation 1. In this case, the TAQMAN™ probe for the reference locus is labeled with the VIC fluorophore and the TAQMAN™ probe for the target locus is labeled with a FAM fluorophore. Thus, equation 1 for each well becomes:

$$\Delta Ct_{ij} = Ct_{ij}^{VIC} - Ct_{ij}^{FAM}$$

1. Calibration delta CTs are calculated for the two reference genes by taking 80% trimmed mean of the plate delta CTs (excluding the control wells) for each reference gene:

$$\Delta Ct_{SMARCC1} = \text{trimmean}(\Delta Ct_{ij}, 80); i \text{ is a } SMARCC1 \text{ well}$$

$$\Delta Ct_{SUPT5} = \text{trimmean}(\Delta Ct_{ij}, 80); i \text{ is a } SUPT5 \text{ well}$$

The trimmed mean for each reference gene is calculated over the wells on the plate that correspond to that reference gene.

2. Calculation of the log call estimates for each well:

$$\log CE_{ij} = 2 + Ct_{ij} - \Delta Ct_{SMARCC1}; i \text{ is a } SMARCC1 \text{ well}$$

$$\log CE = 2 + Ct_{ij} - \Delta Ct_{SUPT5}; i \text{ is a } SUPT5 \text{ well}$$

3. Calculation of call estimates for each well:

$$CE_{ij} = 2^{\log CE_{ij} - 1}$$

4. Call estimates for each sample are calculated by averaging the call estimates for the four sample wells:

$$CE_{Sample_i} = \text{mean}(CE_{ij}); i, j \text{ are the four sample wells}$$

5. Sample calls are calculated by rounding the sample call estimates:

$$C_{Sample_i} = \text{round}(CE_{Sample_i})$$

Example 4

Assays to Determine Mutations at SMN1 Locus

In the present Example, additional assays are performed to determine mutations at the SMN1 locus. The experiments in this example are performed in conjunction with (e.g., before, during, or after on the same set of biological specimens) real-time PCR experiments, such as those described in Example 1. SMN1-specific sequencing is performed with primers that flank the SMN1 amplicon in the real-time PCR experiment to determine if any single-nucleotide polymorphisms (SNPs) or other mutations are responsible for any SMN1 copy number calls of "1" or "0."

After initial PCR amplification, PCR reactions are treated with Exo-SAP (Exonuclease I-shrimp alkaline phosphatase). Each Exo-SAP-purified PCR reaction is sequenced with forward and reverse universal primers UP1 and UP2 to obtain bidirectional sequence information. Sequencing products are electrophoresed through a gel and analyzed on an ABI 3130 sequencing machine, with a 36 cm array and POP6 polymer. Sequence analysis is performed using SEQSCAPE™ software (Applied Biosystems).

Materials and Methods

Sequencing Primers

| Universal Primer | Sequence (5'→3') |
|---|---|
| UP1 | GCGGTCGCATAAGGGTCAGT, (SEQ ID NO: 11) |
| UP2 | CGCCAGCGTATTCCCAGTCA, (SEQ ID NO: 12) |

| PCR Primer | Sequence (5'→3') |
|---|---|
| SMN1FP, (includes UP tag) | GCGGTCGCATAAGGGTCAGTCCATATAAAGCTATCTATATATAGCTATCTATGT, (SEQ ID NO: 13) |
| SMN1RP, (includes UP tag) | CGCCAGCGTATTCCCAGTCATCTTTATTGTGAAAGTATGTTTCTTCCACAT, (SEQ ID NO: 14) |
| SME27FP FAM, (control reaction) | TCGAGTTCAGCCACTGCCAAGTCAGATCCTTTGGAAGGTTGGAT, (SEQ ID NO: 15) |
| SME27RP, (control reaction) | GCTGAAGTCGGTGACGGTTCCATCATCCATGGACCTGCCA, (SEQ ID NO: 16) |

Sequencing PCR Conditions
Step 1: 95° C. for 5 minutes (enzyme denaturation)
Step 2: 95° C. for 30 seconds (denaturation of dsDNA)
Step 3: 63° C. for 20 second (annealing)
Step 4: 72° C. for 1 minutes (extension)
Step 5: Go to step 2, 37 more times
Step 6: 72° C. for 10 minutes (final extension)
Step 7: 8° C. forever
End Example 5

Estimation of SMN1 Allele Frequencies in Major Ethnic Groups within North America Copy number calls as made by methods and systems disclosed herein may be applied to further analyses, for example, estimating allele frequencies in a population.

Spinal Muscular Atrophy (SMA) is the most common inherited lethal disease of children. Various genetic deletions involving the loss of SMN1 exon 7 are reported to account for 94% of mutant alleles that convey this recessive trait. Published literature places the carrier frequency for SMN1 mutations between 1 in 25 and 1 in 50 in the general population. Although SMA is considered to be a pan-ethnic disease, carrier frequencies for specific ethnicities are unknown.

In this example, copy number estimates are obtained as described in Examples 1-3 and then used to estimate allele frequencies in the major ethnic groups in North America. To provide an accurate assessment of SMN1 mutation carrier frequencies in Africa American, Askkenazi, Jewish, Asian, Caucasian, and Hispanic populations, more than 1000 anonymous specimens in each ethnic group were tested using a clinically validated, quantitative real-time PCR assays that measured exon copy number (exon 7 of SMN1). Samples were collected from residual material following routine clinical testing of individuals presumed to have no family history of SMA and were made completely anonymous in accordance with approved protocols. Ethnicities were self reported.

Significant copy number differences were observed between several ethnicities, as shown in Table 4. For one-copy carriers, specimens from individuals of Caucasian or Ashkenazi Jewish ancestry had statistically different frequencies than those from African American and Hispanic backgrounds. For all ethnic groups, except African Americans, the two-copy genotype was more than five times more prevalent than the three-copy. In African Americans, the two- and three-copy genotypes had nearly equal frequency. These unexpected results in the African American group were confirmed by testing a subset (n=50) of the 3-copy samples by an alternate method, Multiplex Ligation-dependent Probe Amplification (MLPA). All MLPA sample results were concordant with the real-time PCR results.

TABLE 4

Frequency of SMN1 copy number across various ethnicities

| Ethnicity | 1 copy | | 2 copies | | 3+ copies | | Total |
| | n | % (95% CI)[1] | n | % (95% CI) | n | % (95% CI) | n |
| --- | --- | --- | --- | --- | --- | --- | --- |
| Caucasian | 28 | 2.7% (1.9%, 3.9%) | 935 | 91.0% (89%, 93%) | 65 | 6.3% (5%, 8%) | 1028 |
| Ashkenazi Jewish | 22 | 2.2% (1.5%, 3.3%) | 827 | 82.5% (80%, 85%) | 153 | 15.3% (13%, 18%) | 1002 |
| Asian | 18 | 1.8% (1.1%, 2.8%) | 897 | 87.3% (85%, 89%) | 112 | 10.9% (9.2%, 13%) | 1027 |
| African American | 11 | 1.1% (0.61%, 1.9%) | 529 | 52.1% (49%, 55%) | 475 | 46.8% (44%, 50%) | 1015 |
| Hispanic | 8 | 0.8% (0.4%, 1.5%) | 870 | 84.5% (82%, 87%) | 152 | 14.8% (13%, 17%) | 1030 |

[1]Confidence interval for genotype frequency estimate

Frequencies of SMN1 copy numbers per allele for each ethnic group were also calculated from the observed genotypes in Table 4. Calculated frequencies assume Hardy-Weinberg equilibrium. and are shown in Table 5.

TABLE 5

Frequencies of SMN1 Copies per allele

| Ethnicity | 0 | 1 | 2 | $1^D$ |
| --- | --- | --- | --- | --- |
| Caucasian | 1.43% | 95.29% | 3.26% | 0.03% |
| Ashkenazi Jewish | 1.21% | 90.72% | 8.06% | 0.02% |
| Asian | 0.94% | 93.38% | 5.67% | 0.02% |
| African American | 0.75% | 71.89% | 27.34% | 0.01% |
| Hispanic | 0.42% | 91.86% | 7.71% | 0.01% |

$1^D$ = disease allele (not caused by SMN1 exon 7 deletion/conversion, e.g., point mutations)
1 = allele with 1 copy of SMN1
2 = allele with 2 or more copies of SMN1

Prevalence of the $1^D$ allele in all ethnic groups was based on the frequency described in SMA patients by Wirth et al. (1999) "Quantitative analysis of survival motor neuron copies: identification of subtle SMN1 mutations in patients with spinal muscular atrophy, genotype-phenotype correlation, and implications for genetic counseling." *Am. J. Hum. Genet.* (64: 1340-1356), the contents of which are herein incorporated by reference.

In conclusion, testing of more than 1000 specimens from five ethnic groups revealed significant differences in many allele frequencies.

Materials and Methods

Calculation of copy number estimates for exon 7 of the SMN1 gene, quality control checks, and statistical checks were performed as described in Examples 1-3 above.

Calculation of Confidence Intervals Around Genotype Frequency Estimates

95% confidence intervals (95% CI) around genotype frequency estimates shown in Table 4 were calculated based on the exact beta distribution model. The allele frequencies shown in Table 5 are maximum likelihood estimates calculated from the observed genotype data under assumption of Hardy-Weinberg equilibrium. An EM algorithm is employed to account for missing observations of the 0 SMN1 copy genotype in the screening population. The algorithm converges to six significant digits in the estimation of the allele frequencies after two iterations. The 95% CI around the allele frequency estimates and the prior risk estimates (Table 5) are calculated as the corresponding percentiles of simulated populations of allele frequencies and risk estimates. These Monte Carlo simulations are based on 10,000 random genotype observations generated from the posterior beta distribution followed by maximum likelihood estimation of the allele frequencies under the Hardy-Weinberg assumption.

Other Embodiments

Other embodiments of the invention will be apparent to those skilled in the art from a consideration of the specification or practice of the invention disclosed herein. It is intended that the specification and examples be considered as exemplary only, with the true scope of the invention being indicated by the following claims.

What is claimed is:

1. A system for analyzing copy number for a target locus comprising:
   (a) a plurality of biological specimens, each individual biological specimen comprising: (i) a target locus; and (ii) one or more reference loci, wherein each of the reference loci comprise a known copy number;
   (b) one or more reagents for amplifying the target locus and the one or more reference loci from the plurality of biological specimens in parallel in a plurality of real-time PCR biological assays to generate detectable signals, such that the level of detectable signals for the target locus and the one or more reference loci correlate with their respective copy numbers; and
   (c) a computer readable medium having computer readable instructions recorded thereon for implementing a method on a computer, said method comprising:
   calculating
   (i) a calibrator based on the determination of the copy number for the target locus and the one or more reference loci for the plurality of biological assays, wherein the calibrator reflects the overall background difference between the target locus and the one or more reference loci across the plurality of biological assays;
   (ii) a copy number estimate for the target locus for each of the plurality of biological assays normalized using the calibrator;
   (iii) a copy number call based on copy number estimates from replicated asssays for each of the plurality of biological specimens; and
   (iv) the quality of the copy number estimates and/or the statistical confidence of the copy number call for the target locus for each individual biological specimen.

2. The system of claim 1, wherein the one or more reference loci comprise SMARCC1 or SUPT5H.

3. The system of claim 1, wherein the target locus comprises an exon of the survival motor neuron gene 1 (SMN1).

4. The system of claim 1, wherein the target locus comprises exon 7 of SMN1.

5. The system of claim 1, wherein the target locus comprises an exon of the survival motor neuron gene 2 (SMN2).

6. The system of claim 1, wherein the target locus is exon 7 of SMN2.

7. The system of claim 1, wherein the computer readable medium has computer readable instructions for configuring a determination module to determine the level of the detectable signals at each amplification cycle.

8. The system of claim 1, wherein the detectable signals are fluorescent signals.

9. The system of claim 1, wherein the step of determining the quality of the copy number estimates comprises generating quality control metrics based on cycle number measurements and the amplification curve slope thereof generated for the one or more reference loci.

10. The system of claim 1, wherein the step of determining the quality of the copy number estimates comprises determining sample coefficient of variation for replicate assays for each of the plurality of biological specimens.

11. The system of claim 1, wherein the step of determining a statistical confidence of the copy number call comprises determining a measurement confidence and comparing the determined measurement confidence to a predetermined threshold limit.

12. The system of claim 1, wherein the step of determining a statistical confidence of the copy number call comprises determining a call confidence and comparing the determined call confidence to a pre-determined threshold limit.

13. The system of claim 1, wherein the computer readable medium further comprises computer readable instructions to determine if any of the plurality of biological assays is failed.

14. The system of claim 1, wherein step (i) comprises first measuring cycle numbers (Cti) for each of the target locus and the one or more reference loci in each of the plurality of biological assays to reach a predetermined level.

15. The system of claim 1, wherein the copy number estimate for the target locus in each individual biological specimen is determined on a linear scale.

16. The system of claim 1, wherein the copy number estimate for the target locus in each individual biological specimen is determined on a logarithmic scale.

17. The system of claim 1, wherein the statistical confidence is assessed by determining a measurement confidence and/or a call confidence.

18. The system of claim 1, wherein the statistical confidence of the copy number call is determined by the calculation of a measurement confidence for replicate biological assays and a call confidence based on the plurality of copy number estimates.

19. The system of claim 1, wherein the copy number call for the target locus cannot be made if the statistical confidence of the copy number call is less than a predetermined threshold.

20. The system of claim 1, wherein calculating copy number estimates for the target locus in each of the plurality of biological specimens comprises the following steps:
 (i) determining the difference in cycle numbers ($\Delta Cti$) between the target locus and the one or more reference loci to reach a pre-determined level of detectable signal for each individual biological specimen;
 (ii) generating a calibrator ($\Delta \tilde{C}t$), wherein the calibrator is calculated from all of the biological assays conducted in parallel and is defined by a trimmed mean of the $\Delta Cti$ between the target locus and the one or more reference loci for the plurality of biological specimens; and
 (iii) determining a copy number estimate for the target locus in each individual biological specimen by normalizing the difference in the cycle numbers $\Delta Cti$ determined at step (i) to the calibrator ($\Delta \tilde{C}t$).

21. The system of claim 1, wherein the computer readable medium includes software for displaying content from a computing module on a display device based in part on the computing and data analysis result for the user, wherein the content comprises a copy number call for the target locus and/or a signal indicating if any of the quality control or statistical confidence analysis is failed.

* * * * *

```
                        SEQUENCE LISTING

<160> NUMBER OF SEQ ID NOS: 23

<210> SEQ ID NO 1
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 1
atagctattt tttttaattc ctttattttc c                                   31

<210> SEQ ID NO 2
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 2
cttactcctt aatttaagga atgtgagca                                      29

<210> SEQ ID NO 3
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 3
agggtttcag acaaaatcaa aagaaggaa g                                    31

<210> SEQ ID NO 4
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 4
agggttttag acaaaatcaa aagaaggaa gg                                   32

<210> SEQ ID NO 5
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 5
aggtaccact ggaattggtt gaa                                            23

<210> SEQ ID NO 6
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 6
catatattaa ccctgtccct taaaagca                                       28
```

<210> SEQ ID NO 7
<211> LENGTH: 27
<212> TYPE: DNA
<213> ORGANISM: Artificial sequence
<220> FEATURE:
<223> OTHER INFORMATION: Synthetic oligonucleotide

<400> SEQUENCE: 7
agtacaaaga agcagcacga gcctctg                                27

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
cacgtgaagg tgattgctgg                                        20

<210> SEQ ID NO 9
<211> LENGTH: 23
<212> TYPE: DNA
<213> ORGANISM: Artificial sequence
<220> FEATURE:
<223> OTHER INFORMATION: Synthetic oligonucleotide

<400> SEQUENCE: 9
cgacccttct atccacctac ctc                                    23

<210> SEQ ID NO 10
<211> LENGTH: 28
<212> TYPE: DNA
<213> ORGANISM: Artificial sequence
<220> FEATURE:
<223> OTHER INFORMATION: Synthetic oligonucleotide

<400> SEQUENCE: 10
cgttatcctg ttctctgacc tcaccatg                               28

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
gcggtcgcat aagggtcagt                                        20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
cgccagcgta ttcccagtca                                        20

<210> SEQ ID NO 13
<211> LENGTH: 54
<212> TYPE: DNA
<213> ORGANISM: Artificial sequence
<220> FEATURE:

<223> OTHER INFORMATION: Synthetic oligonucleotide

<400> SEQUENCE: 13
gcggtcgcat aagggtcagt ccatataaag ctatctatat atagctatct atgt        54

<210> SEQ ID NO 14
<211> LENGTH: 51
<212> TYPE: DNA
<213> ORGANISM: Artificial sequence
<220> FEATURE:
<223> OTHER INFORMATION: Synthetic oligonucleotide

<400> SEQUENCE: 14
cgccagcgta ttcccagtca tctttattgt gaaagtatgt ttcttccaca t           51

<210> SEQ ID NO 15
<211> LENGTH: 44
<212> TYPE: DNA
<213> ORGANISM: Artificial sequence
<220> FEATURE:
<223> OTHER INFORMATION: Synthetic oligonucleotide

<400> SEQUENCE: 15
tcgagttcag ccactgccaa gtcagatcct ttggaaggtt ggat                   44

<210> SEQ ID NO 16
<211> LENGTH: 40
<212> TYPE: DNA
<213> ORGANISM: Artificial sequence
<220> FEATURE:
<223> OTHER INFORMATION: Synthetic oligonucleotide

<400> SEQUENCE: 16
gctgaagtcg gtgacggttc catcatccat ggacctgcca                        40

<210> SEQ ID NO 17
<211> LENGTH: 480
<212> TYPE: DNA
<213> ORGANISM: Homo sapiens

<400> SEQUENCE: 17
tctgatcata ttttgttgaa taaaataagt aaaatgtctt gtgaaacaaa atgcttttta   60
acatccatat aaagctatct atatatagct atctatgtct atatagctat tttttttaac  120
ttcctttatt ttccttacag ggtttcagac aaaatcaaaa agaaggaagg tgctcacatt  180
ccttaaatta aggagtaagt ctgccagcat tatgaaagtg aatcttactt ttgtaaaact  240
ttatggtttg tggaaaacaa atgttttga acatttaaaa agttcagatg ttaaaaagtt  300
gaaaggttaa tgtaaaacaa tcaatattaa agaattttga tgccaaaact attagataaa  360
aggttaatct acatccctac tagaattctc atacttaact ggttggttat gtggaagaaa  420
catactttca caataaagag ctttaggata tgatgccatt ttatatcact agtaggcaga  480

<210> SEQ ID NO 18
<211> LENGTH: 34
<212> TYPE: DNA
<213> ORGANISM: Artificial sequence
<220> FEATURE:
<223> OTHER INFORMATION: Sythetic oligonucleotide

<400> SEQUENCE: 18
ccatataaag ctatctatat atagctatct atgt                              34

```
<210> SEQ ID NO 19
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 19
atagctattt tttttaactt cctttatttt cc                                   32

<210> SEQ ID NO 20
<211> LENGTH: 31
<212> TYPE: DNA
<213> ORGANISM: Artificial sequence
<220> FEATURE:
<223> OTHER INFORMATION: Synthetic oligonucleotide

<400> SEQUENCE: 20
agggtttcag acaaaatcaa aaagaaggaa g                                    31

<210> SEQ ID NO 21
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 21
agggttttag acaaaatcaa aaagaaggaa gg                                   32

<210> SEQ ID NO 22
<211> LENGTH: 29
<212> TYPE: DNA
<213> ORGANISM: Artificial sequence
<220> FEATURE:
<223> OTHER INFORMATION: Synthetic oligonucleotide

<400> SEQUENCE: 22
cttactcctt aatttaagga atgtgagca                                       29

<210> SEQ ID NO 23
<211> LENGTH: 32
<212> TYPE: DNA
<213> ORGANISM: Artificial sequence
<220> FEATURE:
<223> OTHER INFORMATION: Synthetic oligonucleotide

<400> SEQUENCE: 23
ctctttattg tgaaagtatg tttcttccac at                                   32
```